(12) United States Patent
Parng et al.

(10) Patent No.: US 11,358,137 B2
(45) Date of Patent: Jun. 14, 2022

(54) TUBULAR STRUCTURE FOR PRODUCING DROPLETS AND METHOD FOR PRODUCING DROPLETS

(71) Applicant: Industrial Technology Research Institute, Hsinchu (TW)

(72) Inventors: Shaw-Hwa Parng, Kaohsiung (TW); Su-Jan Lee, Taipei (TW); Ping-Jung Wu, Changhua County (TW); Ruey-Shyan Hong, Taoyuan (TW); Yu-Yin Tsai, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 343 days.

(21) Appl. No.: 16/726,940

(22) Filed: Dec. 26, 2019

(65) Prior Publication Data

US 2020/0261903 A1    Aug. 20, 2020

Related U.S. Application Data

(60) Provisional application No. 62/784,841, filed on Dec. 26, 2018.

(51) Int. Cl.
| | |
|---|---|
| *B01L 3/02* | (2006.01) |
| *B01L 3/00* | (2006.01) |
| *C12Q 1/686* | (2018.01) |
| *C12Q 1/68* | (2018.01) |

(52) U.S. Cl.
CPC ............... *B01L 3/0241* (2013.01); *B01L 3/52* (2013.01); *C12Q 1/686* (2013.01); *B01L 2300/087* (2013.01); *B01L 2300/0832* (2013.01)

(58) Field of Classification Search
CPC .. B01L 3/0241; B01L 3/52; B01L 2300/0832; B01L 2300/087; C12Q 1/686; C12Q 1/68
USPC .......................................... 422/502, 500, 50
See application file for complete search history.

(56) References Cited

U.S. PATENT DOCUMENTS

| | | | |
|---|---|---|---|
| 5,759,780 | A | 6/1998 | Parker et al. |
| 5,759,781 | A | 6/1998 | Ward et al. |
| 6,387,626 | B1 | 5/2002 | Shi et al. |
| 6,590,094 | B2 | 7/2003 | Karlou-Eyrisch et al. |
| 6,977,145 | B2 | 12/2005 | Fouillet et al. |
| 7,033,761 | B2 | 4/2006 | Shafer |
| 7,056,513 | B2 | 6/2006 | Cech et al. |

(Continued)

FOREIGN PATENT DOCUMENTS

| | | |
|---|---|---|
| CN | 107513495 | 12/2017 |
| EP | 2856177 | 4/2015 |

(Continued)

OTHER PUBLICATIONS

Parng, Shaw-Hwa et al., A 3D tubular structure with droplet generation and temperature control for DNA amplifcation, Microfuidics and Nanofuidics (2021) 25:56. (Year: 2021).*

(Continued)

*Primary Examiner* — Christine T Mui
(74) *Attorney, Agent, or Firm* — JCIPRNET

(57) ABSTRACT

A tubular structure for producing droplets and a method of using the tubular structure to produce droplets are provided. The tubular structure includes microchannel structures, and is used for droplet generation, droplet collection, nucleic acid amplification and/or in situ droplet detection, etc.

20 Claims, 29 Drawing Sheets

(56) References Cited

U.S. PATENT DOCUMENTS

| | | |
|---|---|---|
| 7,233,393 B2 | 6/2007 | Tomaney et al. |
| 7,294,503 B2 | 11/2007 | Quake et al. |
| 7,303,870 B2 | 12/2007 | Hunter et al. |
| 7,405,823 B2 | 7/2008 | Tomaney et al. |
| 7,417,726 B2 | 8/2008 | Kao et al. |
| 7,429,479 B2 | 9/2008 | Harding |
| 7,460,223 B2 | 12/2008 | Harding |
| 7,586,600 B2 | 9/2009 | Kao et al. |
| 7,715,004 B2 | 5/2010 | Tomaney et al. |
| 7,803,529 B1 | 9/2010 | Cantor et al. |
| 7,816,121 B2 | 10/2010 | Pollack et al. |
| 7,846,666 B2 | 12/2010 | Kurn |
| 7,851,158 B2 | 12/2010 | McKernan |
| 7,883,265 B2 | 2/2011 | Kotler et al. |
| 7,998,436 B2 | 8/2011 | Pollack et al. |
| 8,053,192 B2 | 11/2011 | Bignell et al. |
| 8,053,215 B2 | 11/2011 | Hwang et al. |
| 8,067,176 B2 | 11/2011 | Ohashi |
| 8,089,623 B2 | 1/2012 | Kao et al. |
| 8,133,671 B2 | 3/2012 | Williams et al. |
| 8,182,989 B2 | 5/2012 | Bignell et al. |
| 8,189,186 B2 | 5/2012 | Beer |
| 8,293,470 B2 | 10/2012 | Quake et al. |
| 8,293,471 B2 | 10/2012 | Gregg et al. |
| 8,293,475 B2 | 10/2012 | Okamoto |
| 8,338,166 B2 | 12/2012 | Beer et al. |
| 8,367,976 B2 | 2/2013 | Beer et al. |
| 8,535,889 B2 | 9/2013 | Larson et al. |
| 8,574,835 B2 | 11/2013 | Hinz et al. |
| 8,658,430 B2 | 2/2014 | Miller et al. |
| 8,741,571 B2 | 6/2014 | Rigatti et al. |
| 8,748,094 B2 | 6/2014 | Weitz et al. |
| 8,765,380 B2 | 7/2014 | Berka et al. |
| 8,765,381 B2 | 7/2014 | Rigatti et al. |
| 8,822,150 B2 | 9/2014 | Bignell et al. |
| 8,822,151 B2 | 9/2014 | Sambursky et al. |
| 8,841,071 B2 | 9/2014 | Link |
| 8,841,093 B2 | 9/2014 | Takahashi et al. |
| 8,846,581 B2 | 9/2014 | Gordon et al. |
| 8,852,952 B2 | 10/2014 | Pollack et al. |
| 8,951,721 B2 | 2/2015 | Pollack et al. |
| 8,951,732 B2 | 2/2015 | Pollack et al. |
| 9,017,993 B2 | 4/2015 | Schultz et al. |
| 9,040,288 B2 | 5/2015 | Handique et al. |
| 9,052,298 B2 | 6/2015 | Reed et al. |
| 9,079,148 B2 | 7/2015 | Rigatti et al. |
| 9,080,207 B2 | 7/2015 | Handique et al. |
| 9,091,649 B2 | 7/2015 | Pollack et al. |
| 9,121,047 B2 | 9/2015 | Schultz et al. |
| 9,150,852 B2 | 10/2015 | Samuels et al. |
| 9,150,915 B2 | 10/2015 | Esfandyarpour et al. |
| 9,156,010 B2 * | 10/2015 | Colston, Jr. ........... B01L 3/0241 |
| 9,170,060 B2 | 10/2015 | Beer et al. |
| 9,186,643 B2 | 11/2015 | Griffiths et al. |
| 9,187,783 B2 | 11/2015 | Esfandyarpour et al. |
| 9,213,042 B2 | 12/2015 | Oldham et al. |
| 9,216,392 B2 | 12/2015 | Hindson et al. |
| 9,222,115 B2 | 12/2015 | Marble et al. |
| 9,228,229 B2 | 1/2016 | Olson et al. |
| 9,243,288 B2 | 1/2016 | Ness et al. |
| 9,249,461 B2 | 2/2016 | Hinz et al. |
| 9,259,734 B2 | 2/2016 | Williams et al. |
| 9,266,104 B2 | 2/2016 | Link |
| 9,273,355 B2 | 3/2016 | Shoemaker et al. |
| 9,313,833 B2 | 4/2016 | Beer |
| 9,327,303 B2 | 5/2016 | Wang et al. |
| 9,328,376 B2 | 5/2016 | Hiddessen et al. |
| 9,376,713 B2 | 6/2016 | Bashir et al. |
| 9,388,465 B2 | 7/2016 | Hindson et al. |
| 9,410,171 B2 | 8/2016 | Ortac et al. |
| 9,427,737 B2 | 8/2016 | Heredia et al. |
| 9,433,943 B2 | 9/2016 | Bashir et al. |
| 9,441,266 B2 | 9/2016 | Larson et al. |
| 9,447,459 B2 | 9/2016 | Van Eijk et al. |
| 9,476,856 B2 | 10/2016 | Pamula et al. |
| 9,492,797 B2 | 11/2016 | Makarewicz et al. |
| 9,494,520 B2 | 11/2016 | Link |
| 9,499,812 B2 | 11/2016 | Krishnan et al. |
| 9,499,863 B2 | 11/2016 | Drmanac et al. |
| 9,500,664 B2 | 11/2016 | Ness et al. |
| 9,512,478 B2 | 12/2016 | Bignell et al. |
| 9,533,305 B2 | 1/2017 | Esfandyarpour et al. |
| 9,534,216 B2 | 1/2017 | Link et al. |
| 9,562,837 B2 | 2/2017 | Link |
| 9,580,736 B2 | 2/2017 | Tan et al. |
| 9,581,736 B2 | 2/2017 | Jannard et al. |
| 9,617,589 B2 | 4/2017 | Ramsey et al. |
| 9,624,519 B2 | 4/2017 | Godwin et al. |
| 9,625,454 B2 | 4/2017 | Strey et al. |
| 9,631,230 B2 | 4/2017 | Davies et al. |
| 9,637,799 B2 | 5/2017 | Fan et al. |
| 9,649,635 B2 | 5/2017 | Hiddessen et al. |
| 9,677,069 B2 | 6/2017 | Rigatti et al. |
| 9,689,024 B2 | 6/2017 | Hindson et al. |
| 9,695,468 B2 | 7/2017 | Hindson et al. |
| 9,701,998 B2 | 7/2017 | Hindson et al. |
| 9,719,134 B2 | 8/2017 | Yoon et al. |
| 9,725,758 B2 | 8/2017 | Zengerle et al. |
| 9,725,765 B2 | 8/2017 | Pushkarev et al. |
| 9,738,930 B2 | 8/2017 | Nicol et al. |
| 9,738,931 B2 | 8/2017 | Hahn et al. |
| 9,744,513 B2 | 8/2017 | Viovy et al. |
| 9,745,617 B2 | 8/2017 | Larson et al. |
| 9,745,627 B2 | 8/2017 | van Eijk et al. |
| 9,776,146 B2 | 10/2017 | Schultz et al. |
| 9,790,546 B2 | 10/2017 | Froehlich et al. |
| 9,803,226 B2 | 10/2017 | Diehl et al. |
| 9,816,121 B2 | 11/2017 | Agresti et al. |
| 9,822,393 B2 | 11/2017 | Lowe et al. |
| 9,827,545 B2 | 11/2017 | Gauckler et al. |
| 9,855,559 B2 | 1/2018 | Marble et al. |
| 9,856,525 B2 | 1/2018 | McCoy et al. |
| 9,861,986 B2 | 1/2018 | Pollack et al. |
| 9,896,722 B2 | 2/2018 | Link |
| 9,914,957 B2 | 3/2018 | Hiddessen et al. |
| 9,919,277 B2 | 3/2018 | Griffiths et al. |
| 2013/0252262 A1 | 9/2013 | Srinivasan et al. |
| 2014/0179544 A1 | 6/2014 | Steenblock et al. |
| 2014/0363821 A1 | 12/2014 | Bashir et al. |
| 2015/0167066 A1 | 6/2015 | Link et al. |
| 2015/0211048 A1 | 7/2015 | Ramsey et al. |
| 2015/0253284 A1 | 9/2015 | Sudarsan et al. |
| 2015/0299768 A1 | 10/2015 | Ng et al. |
| 2015/0315631 A1 | 11/2015 | Handique et al. |
| 2015/0329891 A1 | 11/2015 | Tan et al. |
| 2015/0376605 A1 | 12/2015 | Jarosz et al. |
| 2015/0376609 A1 | 12/2015 | Hindson et al. |
| 2016/0194629 A1 | 7/2016 | Hinz et al. |
| 2016/0289670 A1 | 10/2016 | Samuels et al. |
| 2016/0333337 A1 | 11/2016 | Duffy et al. |
| 2016/0370352 A1 | 12/2016 | Murrell et al. |
| 2016/0378916 A1 | 12/2016 | Drmanac et al. |
| 2017/0009274 A1 | 1/2017 | Abate et al. |
| 2017/0058342 A1 | 3/2017 | Welsh |
| 2017/0145499 A1 | 5/2017 | Bignell et al. |
| 2017/0166959 A1 | 6/2017 | Hashimoto et al. |
| 2017/0211140 A1 | 7/2017 | Schmitt et al. |
| 2017/0233797 A1 | 8/2017 | Ramsey et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2017/0356036 A1 | 12/2017 | Davies et al. |
| 2017/0369921 A1 | 12/2017 | Tan et al. |
| 2018/0016634 A1 | 1/2018 | Hindson et al. |
| 2018/0030515 A1 | 2/2018 | Regev et al. |
| 2018/0073069 A1 | 3/2018 | Uehara |
| 2018/0334670 A1 | 11/2018 | Bharadwaj et al. |

FOREIGN PATENT DOCUMENTS

| | | |
|---|---|---|
| TW | 201212451 | 3/2012 |
| TW | I388829 | 3/2013 |

(56) References Cited

FOREIGN PATENT DOCUMENTS

| | | |
|---|---|---|
| TW | 201329230 | 7/2013 |
| WO | 2015086132 | 6/2015 |
| WO | 2017130707 | 8/2017 |

OTHER PUBLICATIONS

Bert Vogelstein, et al.,"Digital PCR", Proc. Natl. Acad. Sci. USA vol. 96, Aug. 1999, pp. 9236-9241.
Richard Williams, et al., "Amplification of complex gene libraries by emulsion PCR", Nature Methods vol. 3 No. 7, Jul. 2006, pp. 545-550.
"Office Action of Taiwan Counterpart Application", dated Oct. 13, 2020, pp. 1-3.

\* cited by examiner

TUBULAR STRUCTURE FOR PRODUCING DROPLETS AND METHOD FOR PRODUCING DROPLETS

CROSS-REFERENCE TO RELATED APPLICATION

This application claims the priority benefit of U.S. provisional application Ser. No. 62/784,841, Dec. 26, 2018. The entirety of the above-mentioned patent application is hereby incorporated by reference herein and made a part of this specification.

BACKGROUND

Technical Field

The disclosure relates to a tubular structure for producing droplets and a method for producing droplets.

Description of Related Art

Droplet digital polymerase chain reaction (ddPCR) is a method of performing absolute quantification for nucleic acid molecules. In a general ddPCR, a droplet generator may be used to divide a sample into hundreds or even tens of thousands of nanoliter level or even picoliter level single water-in-oil droplets. In these droplets, some of the droplets do not contain nucleic acid molecules or only contain a single nucleic acid molecule. Thereafter, PCR amplification is performed on a specimen in the droplets, and then a fluorescent signal is applied to perform detection and statistical analysis. Compared with a conventional quantitative PCR, the digital PCR may demonstrate a high sensitivity, high accuracy and multi-target quantitative ability.

At present, a method of using a commercial ddPCR machine for detection may include following steps. Droplets are generated by using a droplet generator. The generated droplets are placed in a 96-well plate sealer for sealing. The sealed 96-well plate is placed in a PCR machine to perform nucleic acid amplification. The droplets subjected to the nucleic acid amplification are extracted to a droplet detector to perform optical interpretation. Since each operation process is processed in a different container and a different machine, the sample is liable to have some loss during a transfer process and process automation is quite difficult. Meanwhile, the ddPCR process requires a large number of consumables, especially the droplet generator used to generate the droplets, which cannot be reused due to a concern of cross-contamination of specimens, causing the cost of detection to be increased.

At present, there is a lack of product that may be conveniently and accurately used in the ddPCR.

SUMMARY

The disclosure provides a tubular structure for producing droplets and a method of using the tubular structure to produce droplets. The tubular structure of the disclosure has microchannels to separate a water phase reagent, and the water phase reagent forms droplets with a water-in-oil structure through a shearing effect of an oil phase liquid in the tubular structure. Since the tubular structure of the disclosure may produce droplets in a single tubular structure, it occupies less space than an existing multi-slot structure. In some embodiments of the disclosure, the tubular structure of the disclosure may be continuously used for implementing ddPCR or other biochemical reactions after the droplets are produced, and droplet detection or droplet separation may be performed in situ without removing the droplets to another reaction container or machine. In this case, droplet production, subsequent biochemical reaction (such as the PCR), final detection or collection of the droplets, etc., may all be completed in the single tubular structure of the disclosure without replacing a different container consumable or a reaction slot. Therefore, accurate biochemical reaction and/or detection may be performed free of the concern of cross-contamination, by which not only is the cost of the biochemical detection reduced, but the operation is also convenient and an effect of program automation is achieved.

The tubular structure of the disclosure includes an outer tube, a reagent containing region, a first microchannel, an oil filling channel, an exhaust channel, an oil storage region, a droplet containing region, and a second microchannel. The reagent containing region is disposed on a middle portion of an upper portion inside the tubular structure and extends along a tube body length direction. The first microchannel is disposed inside the tubular structure and is located below the reagent containing region. A first end of the first microchannel is connected to the reagent containing region, and the first microchannel communicates with the reagent containing region through the connected first end, and the first microchannel extends along the tube body length direction. The oil filling channel and the exhaust channel are disposed at the upper portion inside the tubular structure and are respectively located at two opposite sides of the reagent containing region, wherein the oil filling channel and the exhaust channel extend along the tube body length direction. The oil storage region is disposed at a lower portion inside the tubular structure, wherein the oil filling channel is connected above the oil storage region and communicates with the oil storage region. The droplet containing region is disposed at the lower portion inside the tubular structure, wherein the exhaust channel is connected above the droplet containing region and communicates with the droplet containing region. The second microchannel is located between the oil storage region and the droplet containing region and is connected to the oil storage region and the droplet containing region, wherein the second microchannel extends along a radial direction perpendicular to the tube body length direction. The first microchannel is vertically connected to the second microchannel through a second end opposite to the first end, and the second microchannel communicates with the oil storage region, the droplet containing region and the first microchannel. A diameter of the first microchannel is less than a diameter of the second microchannel.

The disclosure provides a tubular structure for producing droplets including a reagent containing inner tube and an oil agent containing outer tube. The reagent containing inner tube is disposed at a middle portion inside the tubular structure and extends along a tube body length direction, wherein the reagent containing inner tube has a first cavity to contain a reagent solution and the reagent containing inner tube includes a microwell array located at a lower portion of the reagent containing inner tube. The oil agent containing outer tube is located outside the reagent containing inner tube and surrounds a side portion and the lower portion of the reagent containing inner tube, wherein the oil agent containing outer tube has a second cavity to contain an oil body, the microwell array is located between the reagent containing inner tube and the oil agent containing outer tube, and the reagent solution in the reagent containing inner tube is separated in the oil body in the oil agent containing outer tube to form the droplets through the microwell array.

The disclosure provides a method for producing droplets including following steps. A tubular structure is provided, and the tubular structure includes a reagent containing region, an oil agent containing region, a droplet containing region, and a first microchannel and a second microchannel disposed inside the tubular structure, wherein the first microchannel is connected below the reagent containing region and communicates with the reagent containing region, and the second microchannel is connected between the oil agent containing region and the droplet containing region and communicates with the oil agent containing region and the droplet containing region, the first microchannel is vertically connected to the second microchannel, and the first microchannel and the second microchannel communicate with each other. A reagent solution containing a specimen is added to the reagent containing region. An oil agent is added to the oil agent containing region. The reagent solution is driven to pass through the first microchannel and the oil agent is driven to flow into the second microchannel, such that the oil agent wraps the reagent solution to form the droplets.

Based on the above description, the tubular structure of the disclosure uses a three-dimensional structure formed by intersected three-dimensional perpendicular flow paths of the first microchannel and the second microchannel to construct a droplet generation mechanism on a non-same plane, and produce droplets in the microchannel in a water-in-oil manner. Operations from droplet generation, droplet detection, droplet separation to the final droplet collection may all be completed within a same tubular structure consumable, by which not only are errors of human operations in the detection process reduced, reliability increased and detection functionality improved, but low-cost, accurate and efficient biochemical detection is also achieved due to reduction of the use of consumables and a sample loss.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF THE EMBODIMENTS

Figure 1A:
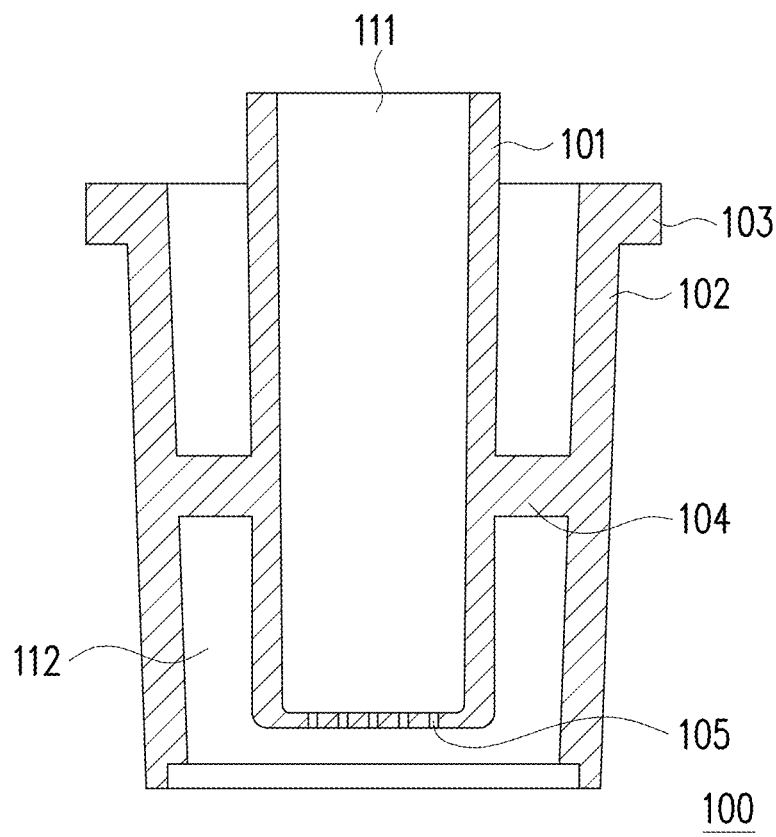
FIG. 1A and FIG. 1B are a cross-sectional view and a top view of a tubular structure according to a first embodiment of the disclosure.

Embodiments are described in detail below with reference to the drawings, but the provided embodiments are not intended to limit a scope covered by the disclosure. In addition, the drawings are for illustrative purposes only, and are not necessarily drawn to scale. For easy understanding, the same devices in the following description will be indicated by the same symbols. In addition, the terms "contain", "include", "have", etc. used in the text are all open terms, which means "include but not limited to". Moreover, directional terminologies, such as "up", "down" etc., mentioned in the text are only used with reference to the orientation of the figure(s) being described and are not intended to be limiting of the disclosure.

In the specification, droplet is a kind of micro drop having an inner-outer double-layer structure, in which an inner layer is a water phase and an outer layer is an oil phase. A volume of the droplet may be, for example, less than about 1 μL (or between about 1 μL and 1 nL or between about 1 μL and 1 pL), less than about 1 nL (or between about 1 nL and 1 pL), or less than about 1 pL (or between about 1 pL and 1 fL), etc. The droplet may have a diameter (or an average diameter) of less than about 1000, 100, 10, or 1 μm, or a diameter (or the average diameter) of about 1000 to 10 μm, etc. The droplet may be spherical or non-spherical. The droplets may respectively wrap a sample to be tested that is not less than a half of the size of the droplet for respective quantitative counting.

In the specification, "reagent solution" refers to a water phase reagent used to form the inner layer of the droplet, which may be formed by, for example, mixing a specimen, water, and/or a PCR reagent. For example, the specimen may include a biological specimen (such as blood, plasma, saliva, semen, ovum, urine), biomolecules, nano particles, viruses, a food specimen or an environmental specimen, etc. For example, the specimen may be nucleic acid fragments (including DNA or RNA, etc.) or templates extracted from human or animal blood, plasma, saliva, semen, ovum, urine, molecular organism, viruses or other sources, or the specimen may be a liquid specimen obtained by digesting and diluting food or traditional Chinese medicinal materials, or an environmental specimen such as drinking water, washing water, irrigation water, etc. The specimen may include, for example, a coloring agent, a fluorescent label, or a magnetic label to facilitate subsequent detection. The PCR reagent may include deoxy-ribonucleotide triphosphated—NTP, magnesium ions, potassium chloride, potassium sulfate, enzyme, primer, probe, buffer, cell tissue lysis buffer, nano particles, etc., but the disclosure is not limited thereto. For example, the reagent solution may also contain fluorescent dye for subsequent detection.

In the specification, "oil agent" refers to a hydrophobic substance used to form the oil phase of the droplet outer layer. The oil agent may include oil with heat resistance, which is, for example, silicone oil, vegetable oil, fluorinated oil such as FC-40, FC-7500, or mineral oil such as alkane, or a combination thereof, but the disclosure is not limited thereto.

Figure 1B:
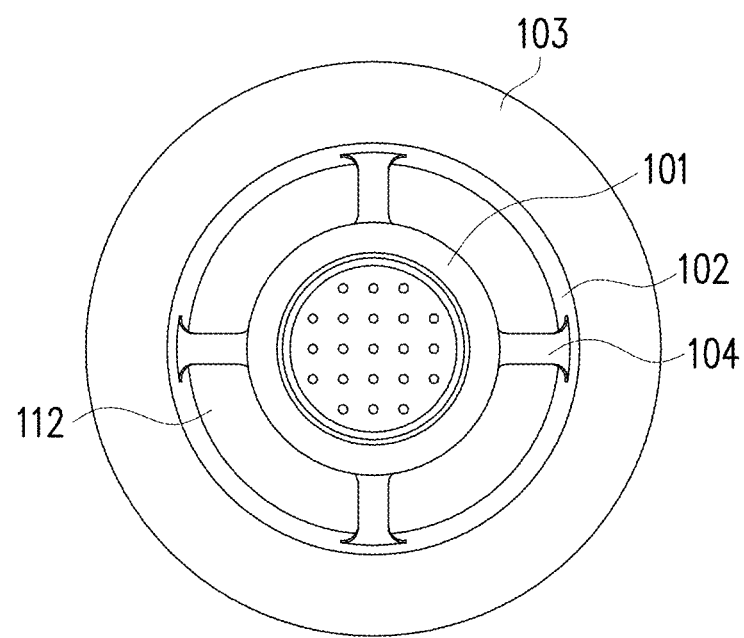

FIG. 1A and FIG. 1B are a cross-sectional view and a top view of a tubular structure according to a first embodiment of the disclosure.

Referring to FIG. 1A and FIG. 1B, the tubular structure 100 of the first embodiment of the disclosure includes a reagent containing inner tube 101 and an oil agent containing outer tube 102, an outer tube support portion 103 and an annular support rib 104. A bottom of the reagent containing inner tube 101 has micropores 105 arranged in an array. A diameter of the micropore may be 0.05 mm to 0.5 mm, which is preferably 0.3 mm. A bottom of the oil agent containing outer tube 102 is a closed structure. The annular support rib 104 is connected to the reagent containing inner tube 101 and the oil agent containing outer tube 102. The outer tube support portion 103 allows the tubular structure 100 to be placed on an experimental carrier to facilitate experimental access.

A method of using the tubular structure 100 to produce droplets includes following steps. A reagent solution is placed in a first cavity 111 of the reagent containing inner tube 101. An oil agent is placed in a second cavity 112 of the oil agent containing outer tube 102. An external driving force such as an air pressure is applied to make the reagent solution in the first cavity 111 to pass through the microarray type micropores 105 to form micro droplets and enter the second cavity 112 to combine with the oil agent in the second cavity 112 to form water-in-oil droplets.

The tubular structure 100 of the first embodiment of the disclosure may be manufactured by, for example, transparent acrylic by using a molding method. In detail, the reagent containing inner tube 101, the oil agent containing outer tube 102 and the annular support rib 104 are respectively manufactured through precision processing, and the manufactured components are combined to form the tubular structure 100, but the disclosure is not limited thereto.

Figure 2A:
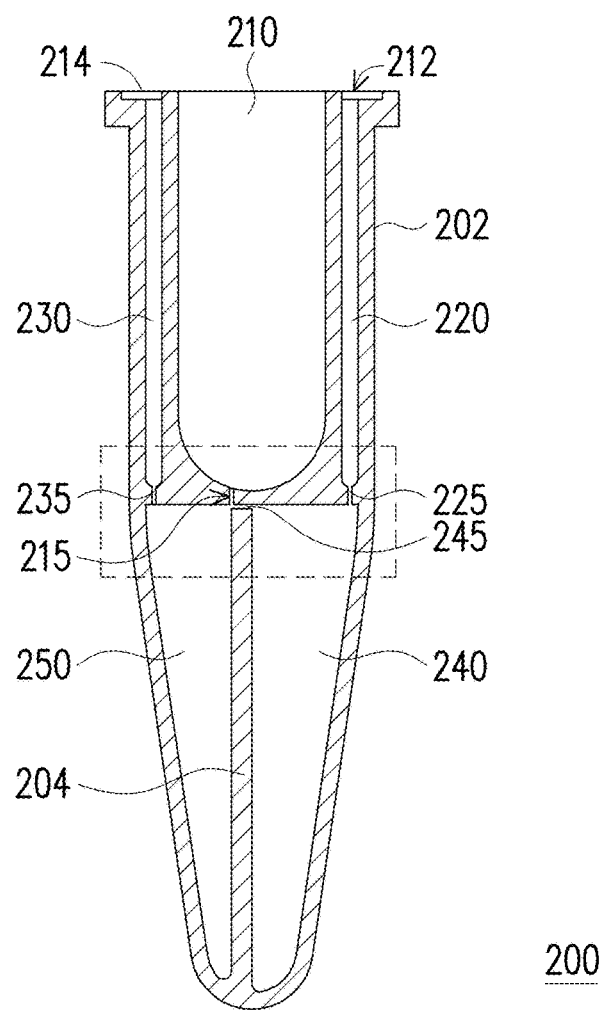
FIG. 2A is a cross-sectional view of a tubular structure according to a second embodiment of the disclosure.
Figure 2B:
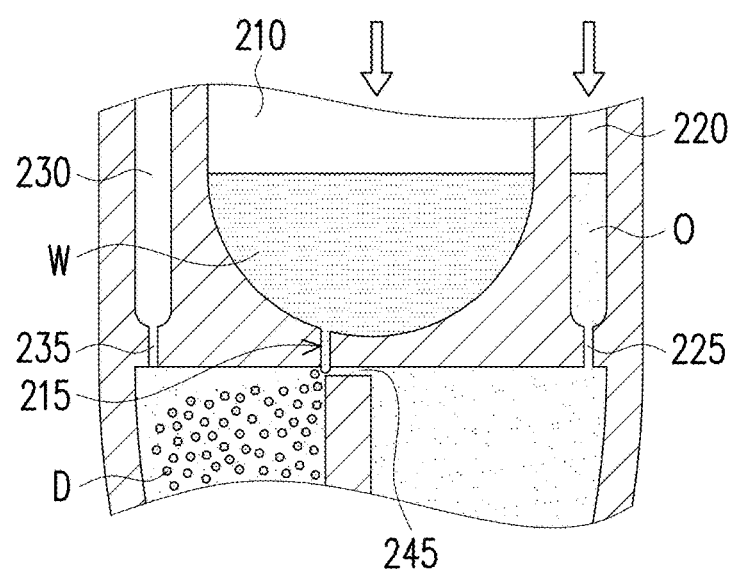
FIG. 2B is a schematic diagram of a method of using the tubular structure of the second embodiment of the disclosure to produce droplets, and FIG. 2B corresponds to a dash line box portion of FIG. 2A.

FIG. 2A is a cross-sectional view of a tubular structure 200 according to a second embodiment of the disclosure. FIG. 2B is a schematic diagram of a method of using the tubular structure of the second embodiment of the disclosure to produce droplets, and FIG. 2B corresponds to a dash line box portion of FIG. 2A.

Referring to FIG. 2A and FIG. 2B, the tubular structure 200 of the second embodiment of the disclosure has an outer tube 202, and the inside of the tube may be divided into an upper portion and a lower portion. The upper portion includes a reagent containing region 210, an oil filling channel 220, an exhaust channel 230, an oil filling hole 212, an exhaust hole 214, a first microchannel 215, an oil region connecting pore canal 225, and a droplet region connecting pore canal 235. The lower portion includes an oil storage region 240, a droplet containing region 250, a second microchannel 245 and a middle partition plate 204. The reagent containing region 210 is disposed in the middle of the upper portion and extends along a tube body length direction. The first microchannel 215 is disposed under the reagent containing region 210. The first microchannel 215 has a first end connected to the reagent containing region 210 and a second end opposite to the first end and connected to the droplet containing region 250, and the second end of the first microchannel 215 is tangent to one end of the second microchannel 245. The oil filling channel 220 and the exhaust channel 230 are respectively located at two opposite sides of the reagent containing region 210 and extend along the tube body length direction. The oil filling hole 212 is formed above the oil filling channel 220. The oil filling channel 220 communicates with the underneath oil storage region 240 through the oil region connecting pore canal 225. The exhaust hole 214 is formed above the exhaust channel 230. The exhaust channel 230 communicates with the underneath droplet containing region 250 through the droplet region connecting pore canal 235. The oil storage region 240 and the droplet containing region 250 are separated by the middle partition plate 204. The second microchannel 245 is formed above the middle partition plate 204. The middle partition plate 204 may be transparent, and extends below the second microchannel 245 along the tube body length direction to a bottom portion of the tubular structure 200. The second microchannel 245 is located at a top surface of the oil storage region 240 and the droplet containing region 250, and extends along a radial direction perpendicular to the tube body length direction. Namely, top surfaces of the second microchannel 245, the oil storage region 240 and the droplet containing region 250 are substantially coplanar. The second microchannel 245 may have a third end connected to the oil storage region 240 and a fourth end opposite to the third end and connected to the droplet containing region 250, and the second end of the first microchannel 215 is vertically connected to the fourth end of the second microchannel 245.

In the embodiment of the disclosure, an inner diameter of the first microchannel 215 may be, for example, 0.05 to 0.5 mm, and an inner diameter of the second microchannel 245 may be, for example, 0.1 to 1 mm. In addition, the inner diameter of the first microchannel 215 may be less than the inner diameter of the second microchannel 245, so that the formed droplet may be completely wrapped by an oil film.

Referring to FIG. 2B, the method of using the tubular structure 200 to produce droplets includes following steps. An oil agent O is injected into the oil filling channel 220 through the oil filling hole 212, and the oil storage region 240 is filled with the oil agent O. A reagent solution W is filled in the reagent containing region 210. A syringe pump is applied to compress air to make the reagent solution W and the oil agent O to respectively pass through the first microchannel 215 and the second microchannel 245, and through outlet fluid pressure shearing of the oil agent O, the oil agent O wraps the reagent solution W to form droplets D. The formed droplets D may be stored in the droplet containing region 250.

Figure 3A:
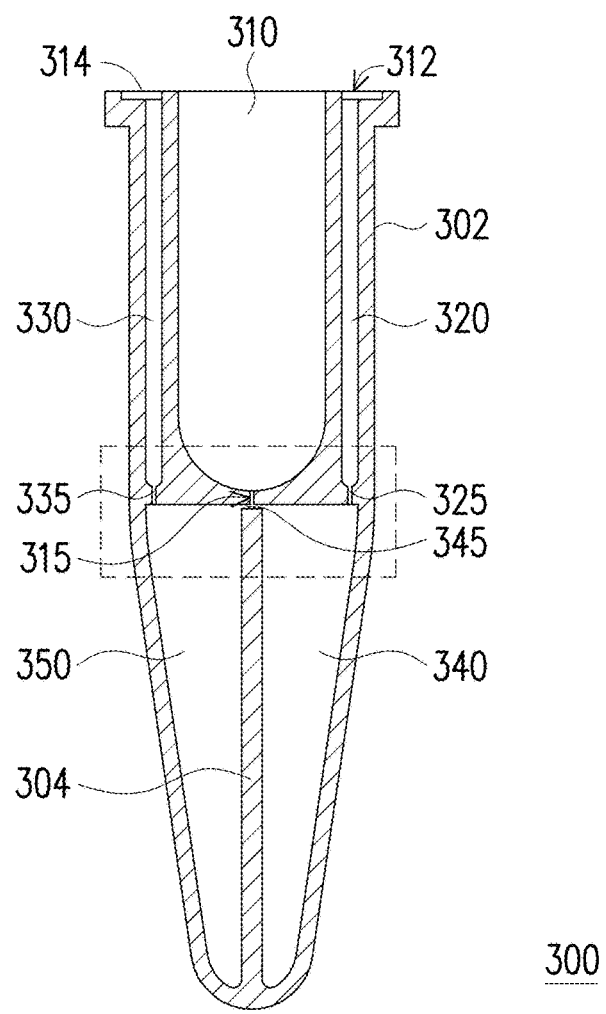
FIG. 3A is a cross-sectional view of a tubular structure according to a third embodiment of the disclosure.
Figure 3B:
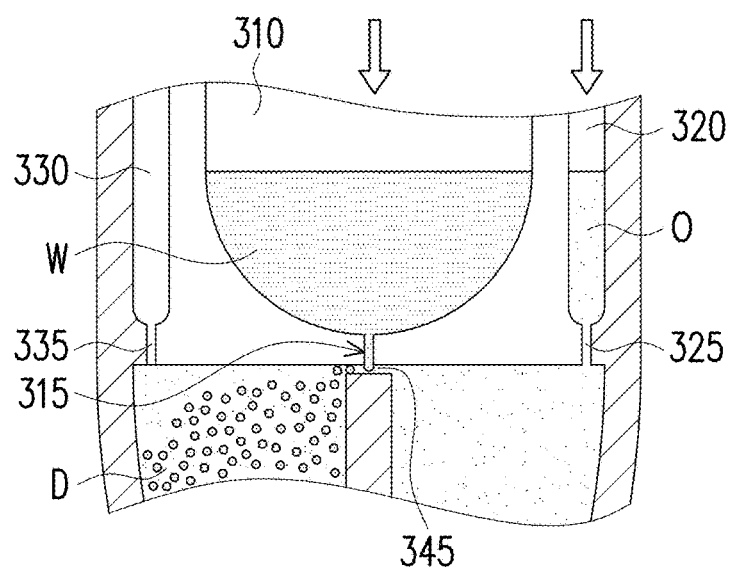
FIG. 3B is a schematic diagram of a method of using the tubular structure of the third embodiment of the disclosure to produce droplets, and FIG. 3B corresponds to a dash line box portion of FIG. 3A.

FIG. 3A is a cross-sectional view of a tubular structure 300 according to a third embodiment of the disclosure. FIG. 3B is a schematic diagram of a method of using the tubular structure of the third embodiment of the disclosure to produce droplets, and FIG. 3B corresponds to a dash line box portion of FIG. 3A.

Referring to FIG. 3A and FIG. 3B, the tubular structure 300 of the third embodiment of the disclosure has an outer tube 302, and the inside of the tube may be divided into an upper portion and a lower portion. The upper portion includes a reagent containing region 310, an oil filling channel 320, an exhaust channel 330, an oil filling hole 312, an exhaust hole 314, a first microchannel 315, an oil region connecting pore canal 325, and a droplet region connecting pore canal 335. The lower portion includes an oil storage region 340, a droplet containing region 350, a second microchannel 345 and a middle partition plate 304. The reagent containing region 310 is disposed in the middle of the upper portion and extends along a tube body length direction. The first microchannel 315 is disposed under the reagent containing region 310. The first microchannel 315 may have a first end connected to the reagent containing region 310 and a second end opposite to the first end and connected to the top of the second microchannel 345, and communicates the reagent containing region 310 with the second microchannel 345. The oil filling channel 320 and the exhaust channel 330 are respectively located at two opposite sides of the reagent containing region 310 and extend along the tube body length direction. The oil filling hole 312 is formed above the oil filling channel 320. The oil filling channel 320 communicates with the underneath oil storage region 340 through the oil region connecting pore canal 325. The exhaust hole 314 is formed above the exhaust channel 330. The exhaust channel 330 communicates with the underneath droplet containing region 350 through the droplet region connecting pore canal 335. The oil storage region 340 and the droplet containing region 350 are separated by the middle partition plate 304. The second microchannel 345 is formed above the middle partition plate 304. The middle partition plate 304 may be transparent, and extends below the second microchannel 345 to the bottom portion of the tubular structure 300 along the tube body length direction. The second microchannel 345 is located at a top surface of the oil storage region 340 and the droplet containing region 350, and extends along a radial direction perpendicular to the tube body length direction. Namely, top surfaces of the second microchannel 345, the oil storage region 340 and the droplet containing region 350 may be substantially coplanar. The second microchannel 345 has a third end connected to the oil storage region 340 and a fourth end opposite to the third end and connected to the droplet containing region 350, and the second end of the first microchannel 315 is vertically connected to a middle portion of the second microchannel 345 between the third end and the fourth end.

In the embodiment of the disclosure, an inner diameter of the first microchannel 315 may be, for example, 0.05 to 0.5 mm, and an inner diameter of the second microchannel 345 may be, for example, 0.1 to 1 mm. In addition, the inner diameter of the first microchannel 315 may be less than the inner diameter of the second microchannel 345, so that the formed droplet may be completely wrapped by the oil film.

Referring to FIG. 3B, the method of using the tubular structure 300 to produce droplets includes following steps. The oil agent O is filled into the oil filling channel 320 through the oil filling hole 312, and the oil storage region 340 is filled with the oil agent O. The reagent solution W is filled in the reagent containing region 310. A syringe pump is applied to compress air to make the reagent solution W to continuously pass through the first microchannel 315 to reach the second microchannel 345 and meet the oil agent O continuously passing through the second microchannel 345 in the second microchannel 345, and due to a difference in surface tensions between the reagent solution W and the oil agent O, the oil agent O wraps the reagent solution W to form the droplets D. The formed droplets D may be stored in the droplet containing region 350.

Figure 4A:
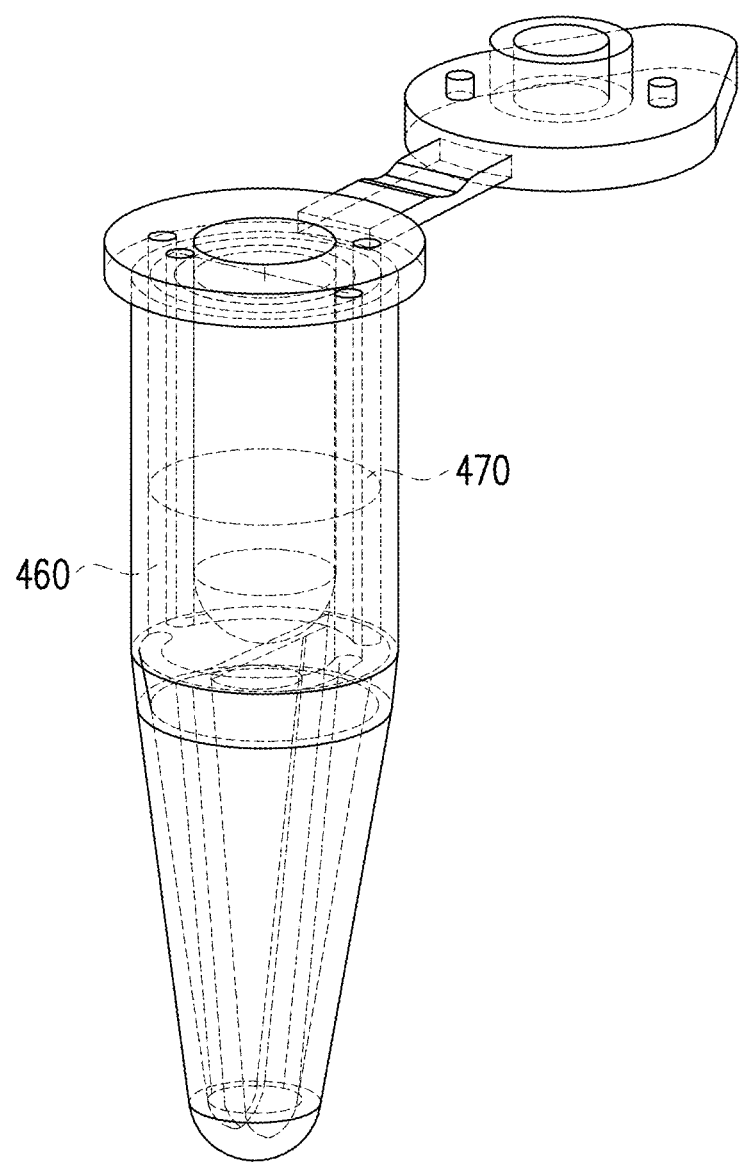
FIG. 4A is a three-dimensional perspective view of a tubular structure according to a fourth embodiment of the disclosure.
Figure 4B:
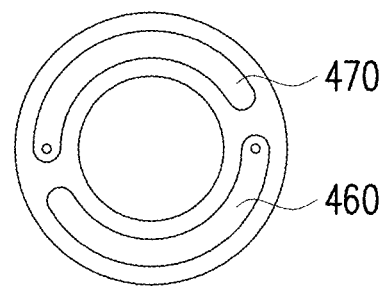
FIG. 4B is a top view of the tubular structure according to the fourth embodiment of the disclosure.
Figure 4C:
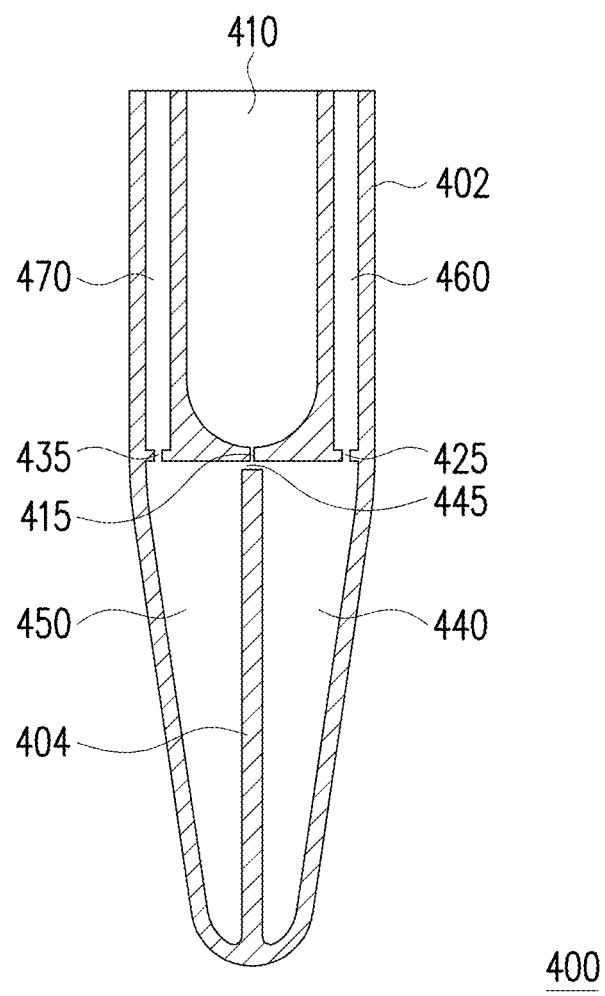
FIG. 4C is a cross-sectional view of the tubular structure according to the fourth embodiment of the disclosure.

FIG. 4A is a three-dimensional perspective view of a tubular structure 400 according to a fourth embodiment of the disclosure. FIG. 4B is a top view of the tubular structure 400 according to the fourth embodiment of the disclosure. FIG. 4C is a cross-sectional view of the tubular structure 400 according to the fourth embodiment of the disclosure.

Referring to FIG. 4A to FIG. 4C, the tubular structure 400 of the fourth embodiment of the disclosure has an outer tube 402, and the inside of the tube may be divided into an upper portion and a lower portion. The upper portion includes a reagent containing region 410, an upper pre-sealed oil storage region 460, an upper droplet containing region 470, a first microchannel 415, an oil region connecting pore canal 425, and a droplet region connecting pore canal 435. The lower portion includes a lower pre-sealed oil storage region 440, a lower droplet containing region 450, a second microchannel 445 and a middle partition plate 404. The reagent containing region 410 is disposed in the middle of the upper portion and extends along the tube body length direction. The first microchannel 415 is disposed under the reagent containing region 410. The first microchannel 415 has a first end connected to the reagent containing region 410 and a second end opposite to the first end and connected to the top of the second microchannel 445, and communicates the reagent containing region 410 with the second microchannel 445. The upper pre-sealed oil storage region 460 and the upper droplet containing region 470 are respectively located at two opposite sides of the reagent containing region 410 and extend along the tube body length direction. As shown in FIG. 4B, when observing from the top of the tubular structure 400, the upper pre-sealed oil storage region 460 and the upper droplet containing region 470 may have arc shapes or half-moon shapes. Therefore, compared with the tubular oil filling channel of the tubular structure 200 of the second embodiment or the tubular oil filling channel of the tubular structure 300 of the third embodiment, more oil agent may be filled. The upper pre-sealed oil storage region 460 communicates with the underneath lower pre-sealed oil storage region 440 through the oil region connecting pore canal 425. The upper droplet containing region 470 communicates with the underneath lower droplet containing region 450 through the droplet region connecting pore canal 435. The lower pre-sealed oil storage region 440 and the lower droplet containing region 450 are separated by the middle partition plate 404. The second microchannel 445 is formed above the middle partition plate 404. The middle partition plate 304 may be transparent, and extends below the second microchannel 445 to a bottom portion of the tubular structure 400 along the tube body length direction. The second microchannel 445 is located at a top surface of the lower pre-sealed oil storage region 440 and the lower droplet containing region 450, and extends along a radial direction perpendicular to the tube body length direction. Namely, top surfaces of the second microchannel 445, the lower pre-sealed oil storage region 440 and the lower droplet containing region 450 may be substantially coplanar. The second microchannel 445 may have a third end connected to the lower pre-sealed oil storage region 440 and a fourth end opposite to the third end and connected to the lower droplet containing region 450, and the second end of the first microchannel 415 is vertically connected to a middle portion of the second microchannel 445 between the third end and the fourth end.

In the embodiment of the disclosure, an inner diameter of the first microchannel 415 may be, for example, 0.05 to 0.5 mm, and an inner diameter of the second microchannel 445 may be, for example, 0.1 to 1 mm. In addition, the inner diameter of the first microchannel 415 may be less than the inner diameter of the second microchannel 445, so that the formed droplet may be completely wrapped by the oil film.

The tubular structure 400 is similar to the tubular structure 300, and the difference there between is that the tubular structure 400 further includes the upper droplet containing region 470 and the upper pre-sealed oil storage region 460. Therefore, when the tubular structure 400 is used to produce droplets, the oil agent has been pre-sealed in the pre-sealed oil storage structure, and the reagent solution may be directly filled in the reagent containing region 410, and the syringe pump is used to compress air to simultaneously drive the reagent solution in the reagent containing region and the oil agent in the pre-sealed oil storage structure without injecting the oil agent from the outside. In addition, the generated droplets may be respectively stored in the upper droplet containing region 470 and the lower droplet containing region 450.

Figure 5A:
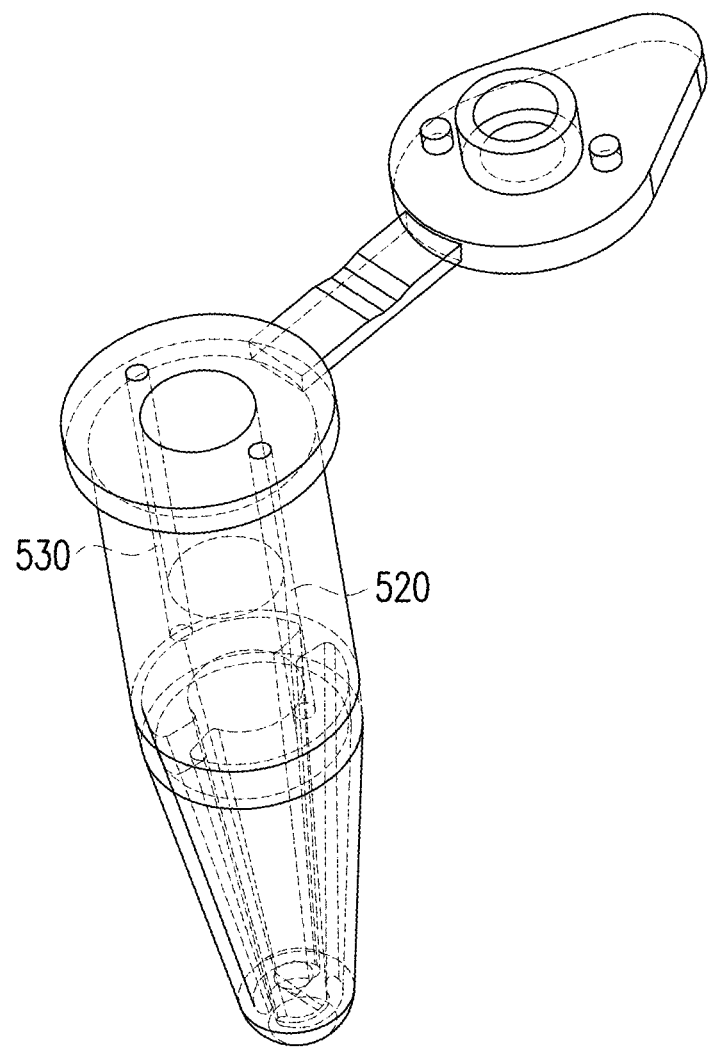
FIG. 5A is a three-dimensional perspective view of a tubular structure according to a fifth embodiment of the disclosure.
Figure 5B:
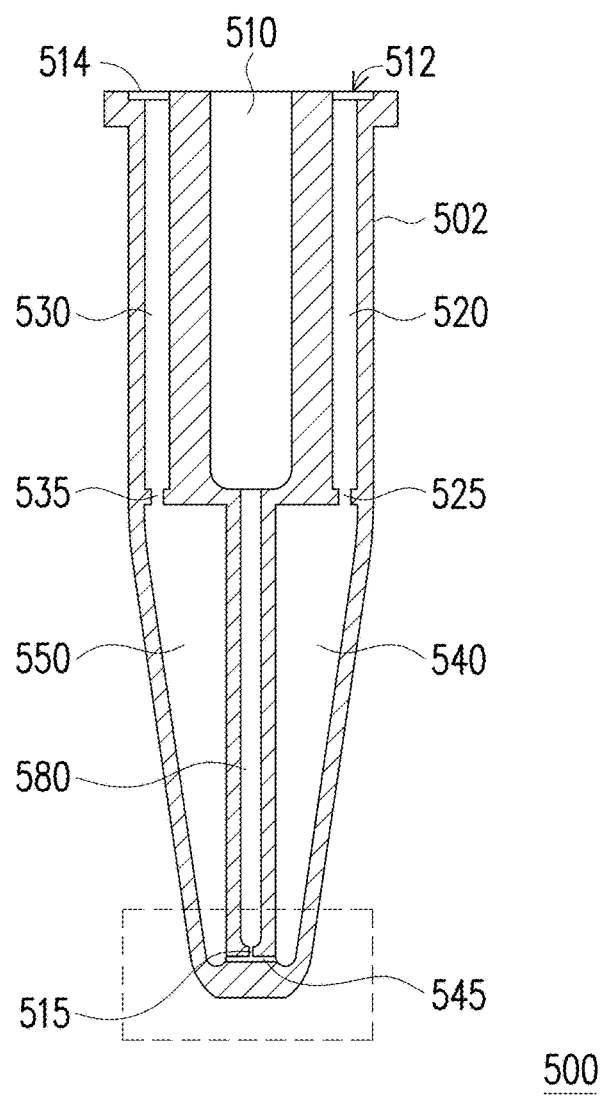
FIG. 5B is a cross-sectional view of the tubular structure according to the fifth embodiment of the disclosure.
Figure 5C:
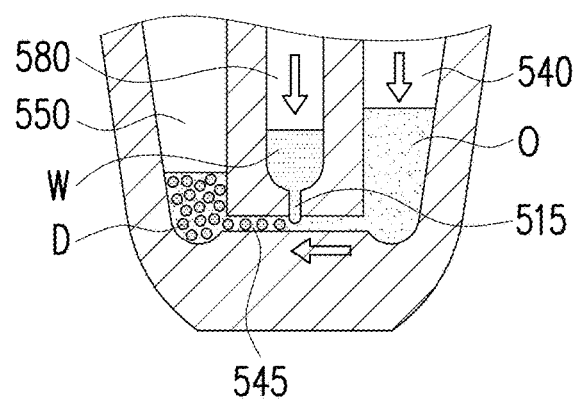
FIG. 5C is a schematic diagram of a method of using the tubular structure of the fifth embodiment of the disclosure to produce droplets, and FIG. 5C corresponds to a dash line box portion of FIG. 5B.

FIG. 5A is a three-dimensional perspective view of a tubular structure 500 according to a fifth embodiment of the disclosure. FIG. 5B is a cross-sectional view of the tubular structure 500 according to the fifth embodiment of the disclosure. FIG. 5C is a schematic diagram of a method of using the tubular structure of the fifth embodiment of the disclosure to produce droplets. FIG. 5C corresponds to a dash line box portion of FIG. 5B.

Referring to FIG. 5A and FIG. 5B, the tubular structure 500 of the third embodiment of the disclosure has an outer tube 502, and the inside of the tube may be divided into an upper portion and a lower portion. The upper portion includes an upper reagent containing region 510, an oil filling channel 520, an exhaust channel 530, an oil filling hole 512, an exhaust hole 514, an oil region connecting pore canal 525 and a droplet region connecting pore canal 535. The lower portion includes an oil storage region 540, a droplet containing region 550, a lower reagent containing region 580, a first microchannel 515 and a second microchannel 545. The upper reagent containing region 510 and the lower reagent containing region 580 are respectively disposed in the middle of the upper portion and in the middle of the lower portion, and extend along the tube body length direction. The upper reagent containing region 510 and the lower reagent containing region 580 communicate with each other. An inner diameter of the upper reagent containing region 510 may be greater than an inner diameter of the lower reagent containing region 580. The oil filling channel 520 and the exhaust channel 530 are respectively located at two opposite sides of the upper reagent containing region 510 and extend along the tube body length direction. The oil filling hole 512 is formed above the oil filling channel 520. The oil filling channel 520 communicates with the underneath oil storage region 540 through the oil region connecting pore canal 525. The exhaust hole 514 is formed above the exhaust channel 530. The exhaust channel 530 communicates with the underneath droplet containing region 550 through the droplet region connecting pore canal 535. The oil storage region 540 and the droplet containing region 550 are disposed at two opposite sides of the lower reagent containing region 580. The first microchannel 515 is disposed under the lower reagent containing region 580 and between the oil storage region 540 and the droplet containing region 550, and extends to the bottom portion of the tubular structure along the tube body length direction to connect the second microchannel 545. The first microchannel 515 has a first end connected to the bottom of the lower reagent containing region 580 and a second end opposite to the first end and connected to the top of the second microchannel 545, and communicates the lower reagent containing region 580 with the second microchannel 545. The second microchannel 545 is located at the bottom inside the tubular structure, and extends along a radial direction perpendicular to the tube body length direction. The second microchannel 545 may have a third end connected to the oil storage region 540 and a fourth end connected to the droplet containing region 550, and the second end of the first microchannel 515 is vertically connected to a middle portion of the second microchannel 545 between the third end and the fourth end.

The bottom portion of the tubular structure 500 may be a smooth and flat surface so that a detection module below the tubular structure 500 may directly detect the droplets in the second microchannel 545 through the bottom portion of the tubular structure 500.

In the embodiment of the disclosure, an inner diameter of the first microchannel 515 may be, for example, 0.05 to 0.5 mm, and an inner diameter of the second microchannel 545 may be, for example, 0.1 to 1 mm. In addition, the inner diameter of the first microchannel 515 may be less than the inner diameter of the second microchannel 545, so that the formed droplet may be completely wrapped by the oil film.

A method of using the tubular structure 500 to produce droplets is similar to the method of using the tubular structure 300 to produce droplets, and a difference there between is that the first microchannel 515 and the second microchannel 545 are arranged near a bottom plane, which facilitates direct detection after the formation of the droplets, and facilitates real-time adjustment of parameters such as a fluid-driven flow rate, etc. The droplets flow into the droplet containing region 550 after being produced, and an optical detection system may be disposed under the second microchannel 545, and whether any droplet has passed the second microchannel 545 may be determined through real-time detection of the optical detection system, so as to adjust the pressure driving system in real-time. After the droplets are produced, the tubular structure 500 may be subjected to a temperature control cycle to make a specimen in the droplets to carry out a polymerase chain reaction (PCR) to amplify the specimen in the droplets. For example, the temperature control cycle of the tubular structure 500 may be carried out by using a carrier with a heating function, but the disclosure is not limited thereto. After the PCR is ended, the pressure driving system may push the droplets to make the droplets to move from the droplet containing region 550 to the oil storage region 540 through the second microchannel 545. Therefore, the optical detection system may be again used to perform optical signal detection on the droplets passing through the second microchannel 545.

Namely, the steps such as droplet generation of the ddPCR, polymerase chain reaction, droplet detection, etc., may all be performed in the tubular structure 500 of the fifth embodiment of the disclosure without replacing consumables, so that a procedure of the ddPCR may be simplified to reduce the cost.

Figure 6A:
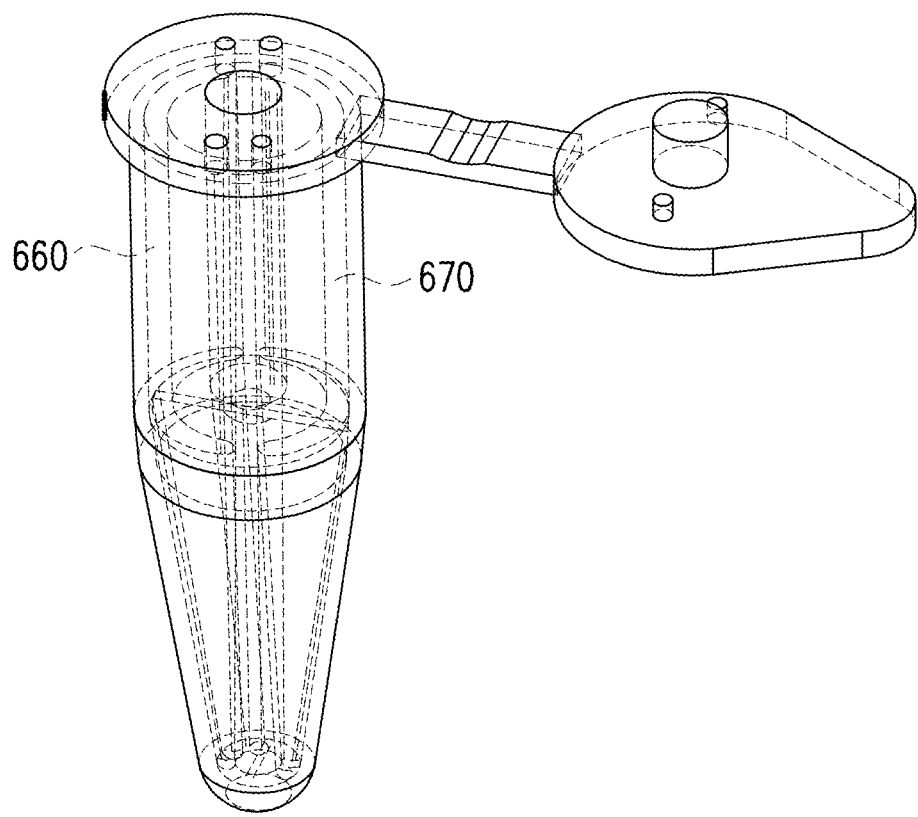
FIG. 6A is a three-dimensional perspective view of a tubular structure according to a sixth embodiment of the disclosure.
Figure 6B:
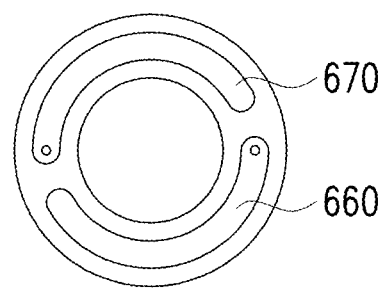
FIG. 6B is a top view of the tubular structure according to the sixth embodiment of the disclosure.
Figure 6C:
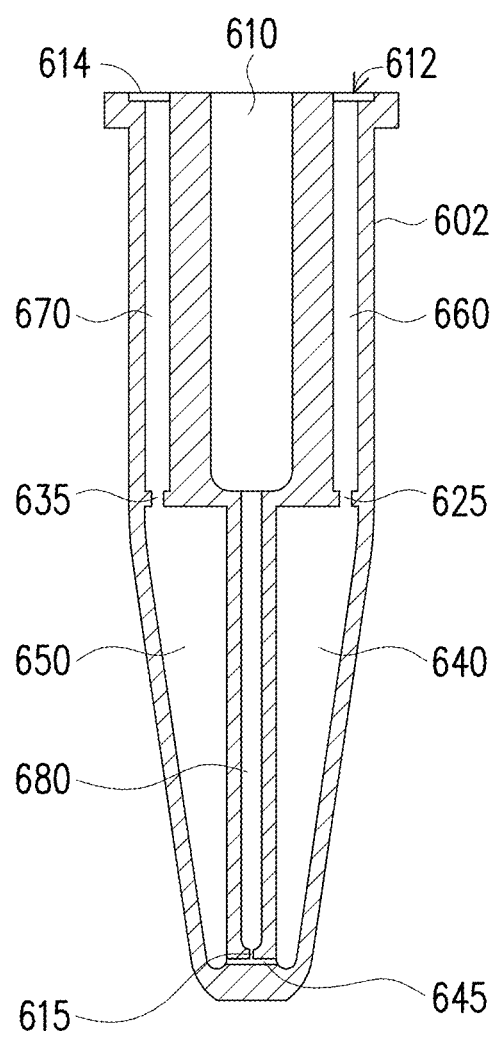
FIG. 6C is a cross-sectional view of the tubular structure according to the sixth embodiment of the disclosure.

FIG. 6A is a three-dimensional perspective view of a tubular structure 600 according to a sixth embodiment of the disclosure. FIG. 6B is a top view of the tubular structure 600 according to the sixth embodiment of the disclosure. FIG. 6C is a cross-sectional view of the tubular structure 600 according to the sixth embodiment of the disclosure.

Referring to FIG. 6A to FIG. 6C, the tubular structure 600 of the sixth embodiment of the disclosure has an outer tube 602, and the inside of the tube may be divided into an upper portion and a lower portion. The upper portion includes an upper reagent containing region 610, an upper pre-sealed oil storage region 660, an upper droplet containing region 670, an oil filling hole 612, an exhaust hole 614, an oil region connecting pore canal 625, and a droplet region connecting pore canal 635. The lower portion includes a lower pre-sealed oil storage region 640, a lower droplet containing region 650, a lower reagent containing region 680, a first microchannel 615 and a second microchannel 645. The upper reagent containing region 610 and the lower reagent containing region 680 are respectively disposed in the middle of the upper portion and in the middle of the lower portion, and extend along the tube body length direction. The upper reagent containing region 610 and the lower reagent containing region 680 communicate with each other. An inner diameter of the upper reagent containing region 610 may be greater than an inner diameter of the lower reagent containing region 680. The upper pre-sealed oil storage region 660 and the upper droplet containing region 670 are respectively located at two opposite sides of the upper reagent containing region 610 and extend along the tube body length direction. When observing from the top of the tubular structure 600, the upper pre-sealed oil storage region 660 and the upper droplet containing region 670 may have circular arc shapes or half-moon shapes. The oil filling hole 612 is formed above the upper pre-sealed oil storage region 660. The bottom of the upper pre-sealed oil storage region 660 communicates with the underneath lower pre-sealed oil storage region 640 through the oil region connecting pore canal 625. The upper droplet containing region 670 has the exhaust hole 614. The bottom of the upper droplet containing region 670 communicates with the underneath lower droplet containing region 650 through the droplet region connecting pore canal 635. The lower pre-sealed oil storage region 640 and the lower droplet containing region 650 are disposed at two opposite sides of the lower reagent containing region 680. The first microchannel 615 is disposed under the lower reagent containing region 680 and between the lower pre-sealed oil storage region 640 and the lower droplet containing region 650, and extends to the bottom portion inside the tubular structure along the tube body length direction to connect the second microchannel 645. The first microchannel 615 has a first end connected to the lower reagent containing region 680 and a second end opposite to the first end and connected to the top of the second microchannel 645, and communicates the lower reagent containing region 680 with the second microchannel 645. The second microchannel 645 is located at the bottom portion inside the tubular structure, and extends along a radial direction perpendicular to the tube body length direction. The second microchannel 645 has a third end connected to the lower droplet containing region 650 and a fourth end opposite to the third end and connected to the lower pre-sealed oil storage region 640, and the second end of the first microchannel 615 is vertically connected to a middle portion of the second microchannel 645 between the third end and the fourth end.

The bottom portion of the tubular structure 600 may be a smooth and flat surface so that a detection module below the tubular structure 600 may directly detect the droplets in the second microchannel 645 through the bottom portion of the tubular structure 600.

In the embodiment of the disclosure, an inner diameter of the first microchannel 615 may be, for example, 0.05 to 0.5 mm, and an inner diameter of the second microchannel 645 may be, for example, 0.1 to 1 mm. In addition, the inner diameter of the first microchannel 615 may be less than the inner diameter of the second microchannel 645, so that the formed droplet may be completely wrapped by the oil film.

A method of using the tubular structure 600 to produce droplets is similar to the method of using the tubular structure 400 to produce droplets, and a difference there between is that the first microchannel 615 and the second microchannel 645 are arranged near a bottom plane, which facilitates direct detection after the droplets are formed, and facilitates real-time adjustment of parameters such as a fluid-driven flow rate, etc. The droplets flow into the lower droplet containing region 650 after being produced. An optical detection system may be disposed under the second microchannel 645, and whether any droplet has passed the second microchannel 645 may be determined through real-time detection of the optical detection system, so as to adjust the pressure driving system in real-time. After the droplets are produced, the tubular structure 600 may be subjected to a temperature control cycle to make a specimen in the droplets to carry out a PCR to amplify the specimen in the droplets. For example, the temperature control cycle of the tubular structure 600 may be carried out by using a carrier with a heating function, but the disclosure is not limited thereto. After the PCR is ended, the pressure driving system may push the droplets to make the droplets to move from the lower droplet containing region 650 to the lower pre-sealed oil storage region 640 through the second microchannel 645. Therefore, the optical detection system may be again used to perform optical signal detection on the droplets passing through the second microchannel 645.

Namely, the steps such as droplet generation of the ddPCR, polymerase chain reaction, droplet detection, etc., may all be performed in the tubular structure 600 of the sixth embodiment of the disclosure without replacing consumables, so that the procedure of the ddPCR may be simplified to reduce the cost.

Referring to FIG. 4A, FIG. 5A and FIG. 6A, each of the tubular structures of the embodiments of the disclosure may also include an outer cover that may be mated to a top portion of the tubular structure to avoid cross-contamination, prevent spilling, and facilitate storage and transportation. The outer cover of the disclosure is not particularly limited and may have various forms. The outer covers in the figures are only examples, and the outer covers of the tubular structures in the embodiments of the disclosure are not limited thereto.

The tubular structures according to the embodiments of the disclosure may be formed by a polymer material. For example, the polymer material may be acrylonitrile-butadiene-styrene (ABS) copolymer, acrylonitrile-styrene resin (AS), bulk molding compound (BMC), cellulose acetate (CA), cellulose nitrate (CN), cyclo-olefin copolymer (COC), cyclo-olefin polymer (COP), ethyl cellulose (EC), epoxy resin (EP), ethylene vinyl acetate copolymer (EVA), perfluoro(ethylene-propylene) (FEP) plastic, fiber reinforced plastics (FRP), melamine formaldehyde resin (MF), polymethylmethacrylate (PMMA), polyamide (PA), polyarylate (PAR), polybutene (PB), poly(butylene terephthalate) (PBT), polycarbonate (PC), polydimethylsiloxane (PDMS), low density polyethylene (LDPE), high density polyethylene (HDPE), polymer ethylene (PE), poly(ether-ether-ketone) (PEEK), polyethylene terephthalate (PET), poly(ether sulfone) (PES), phenol-formaldehyde resin (PF), polyoxymethylene (POM), polypropylene (PP), polyphenylene oxide (PPO), poly(p-phenylene sulfide) (PPS), high impact polystyrene (HIPS), polystyrene (PS), poly sulfone (PSF), poly (tetrafluoroethylene) (PTFE), polyurethane (PU), polyvinyl alcohol (PVA), poly(vinyl acetate) (PVAC), poly(vinyl butyral) (PVB), polyvinyl chloride (PVC), polyvinyl chloride acetate (PVCA), polyvinylidene chloride (PVDC), polyvinyl formal (PVFM), saturated polyester (SP), urea formaldehyde resin (UF), unsaturated polyester (UP) or any combination thereof, but the disclosure is not limited thereto. The formed tubular structure may be transparent.

The tubular structures of the embodiments of the disclosure may be obtained by a general molding method such as blow molding, extrusion molding, pressure molding, injection molding, etc. The tubular structures of the embodiments of the disclosure may be manufactured by respectively manufacturing individual components and bonding the components together. For example, an upper portion component, a lower portion component, and the outer cover of the tubular structure may be respectively manufactured and then the components are bonded. There is no particular limitation on a bonding method of each of the components. For example, the bonding method may be hot-melt bonding, ultrasonic bonding, UV hardening, chemical bond bonding, adhesive bonding, tenon bonding, etc., but the disclosure is not limited thereto.

In the embodiments of the disclosure, a liquid driving module may be arranged above each of the tubular structures to serve as a power source to push the reagent solution and the oil agent in the tubular structure to pass through the microchannels through air, so as to make the oil agent wrapping the reagent solution in the second microchannel or the droplet containing region to form reagent-in-oil droplets. For example, the liquid driving module may include, for example, a power source such as a syringe pump, a peristaltic pump, etc. to push the air to drive the reagent solution and the oil agent in the tubular structure to form the droplets. In another embodiment, the tubular structure may be heated, and the air inside the tubular structure may drive the reagent solution and the oil agent. For example, the method for producing droplets of the disclosure may include using a heat source to drive the air while heating the reagent containing region and the oil filling channel, wherein the internal air simultaneously drives the reagent solution and the oil agent, and the oil agent wraps the reagent solution in the second microchannel to form the reagent-in-oil droplets.

In the embodiments of the disclosure, a detection module may be arranged below each of the tubular structures to detect the droplets in the tubular structure in real-time. To be specific, the detection module may directly detect the droplets in the second microchannel through the flat transparent bottom of the tubular structure. For example, electromagnetic field detection or optical detection may be used to detect the droplets. The electromagnetic field detection includes detecting an electromagnetic field signal intensity of the droplets by using a magnetic field, an electric field, and electromagnetic waves. The optical detection includes detecting a signal intensity of the droplets by using cold light, absorption light, fluorescent light, etc. To be specific, the detection module may be, for example, an optical microscope or a spectrum analyzer, but the disclosure is not limited thereto. The detection module may detect a droplet generation state in real-time when the droplets are produced, so as to adjust the parameters of the liquid drive module. Regarding the specimen that requires PCR amplification, the liquid driving module may be used to drive the droplets to pass through the second microchannel from the droplet containing region to implement the real-time detection after the PCR. Alternatively, quantitative concentration interpretation is performed on diluted specimen that does not require the PCR amplification.

For example, when it is required to detect trace pesticide molecules in a food specimen or an environmental specimen, Raman spectroscopy may be used to detect Raman scattering of the droplet to quantify the trace pesticide molecules in the droplet to determine a pesticide residue. When it is required to detect a trace metal in a food specimen or an environmental specimen, a coloring agent may be added to the specimen to react with the metal in the specimen to form a colored substance. Then, the tubular structure of the disclosure is used to produce droplets. A photometer is used to measure an absorption light intensity of the droplet to quantify a concentration of the trace metal in the droplet to determine content of heavy metal.

In the embodiment of the disclosure, the carrier carrying the tubular structure may have a temperature control function. The carrier may be used to heat the reagent storage region and the oil filling channel in the tubular structure during a droplet producing period to drive the reagent solution and the oil agent, or after the droplets are produced in the tubular structure, the carrier may be used to directly perform temperature control on the tubular structure to make the droplets in the tubular structure to carry on the PCR for amplification.

The disclosure is described in detail in the following examples. However, the following examples are only provided to describe the disclosure, and the disclosure is not limited to the following examples.

Example 1: A Middle Type Microchannel Pre-Sealed Oil Slot Tubular Structure

The middle type microchannel pre-sealed oil slot tubular structure of the fourth embodiment of the disclosure is manufactured through injection molding. A material thereof is polypropylene, and a finished product is divided into three parts: an upper part, a middle part, and a lower part, an outer diameter of the tubular structure is 6 mm, and the three parts are bonded through ultrasonic welding in the middle for integration. Referring to FIG. 4A, the tubular structure of the example 1 has an outer cover. The outer cover is a sealing cover with a foldable structure. There are a reagent hole sealing sleeve, sealing sleeves of the oil filling hole and the exhaust hole on the top of the structure, which may seal the reagent containing region, the oil filling channel, and the exhaust channel when the outer cover is closed to prevent contamination during a detection process. The upper portion of the tubular structure includes the reagent containing region, the first microchannel, the upper pre-sealed oil storage region and the upper droplet containing region. The lower portion of the tubular structure includes the lower pre-sealed oil storage region, the second microchannel, the middle partition plate and the lower droplet containing region.

Figure 7A:
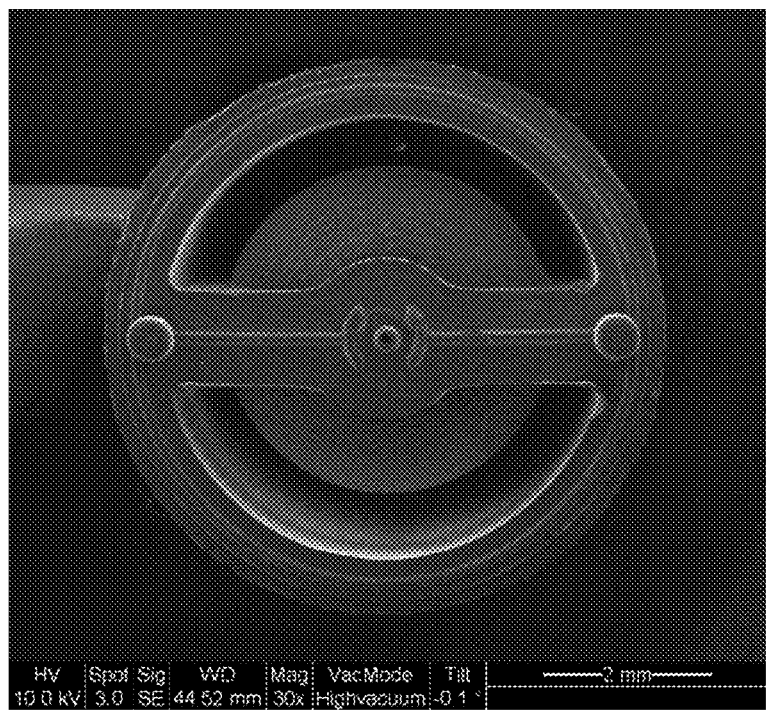
FIG. 7A and FIG. 7B are respectively electron micrographs of a lower surface of an upper portion and an upper surface of a lower portion of a tubular structure of an example 1.
Figure 7B:
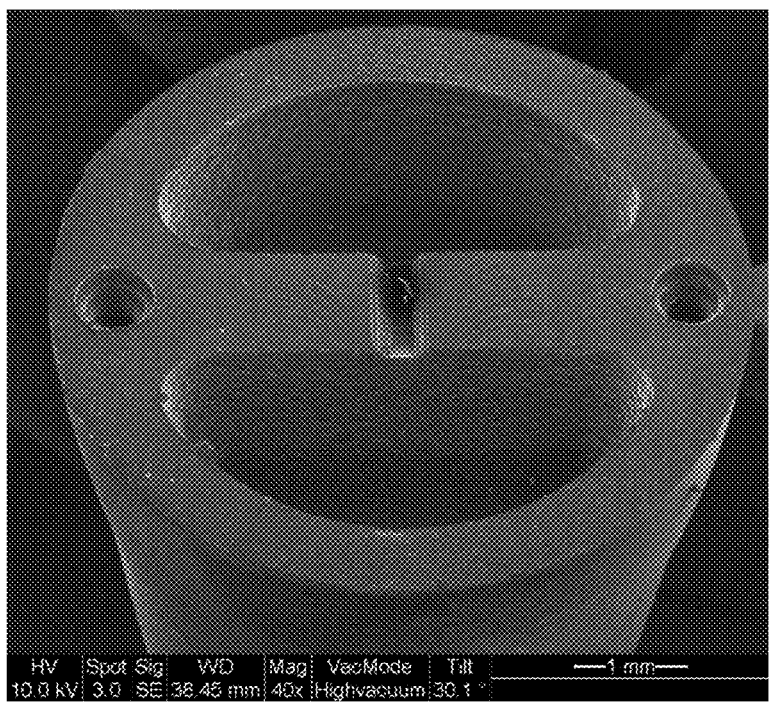

FIG. 7A and FIG. 7B are respectively electron micrographs of a lower surface of the upper portion and an upper surface of the lower portion of the tubular structure of the example 1. Referring to FIG. 7A, the upper portion of the tubular structure of the example 1 has the middle partition plate to partition the upper pre-sealed oil storage region and the upper droplet containing region, and a through-hole (i.e. the first microchannel) with a diameter of 0.1 mm is formed above the middle partition plate to connect the reagent containing region. An ultrasonic welding structure is arranged above a cross region of a tube wall to bond the lower portion of the tubular structure, and there are protruding positioning pins on the cross section of the tube wall for positioning before ultrasonic bonding. Referring to FIG. 7B, the lower portion of the tubular structure has the middle partition plate to partition the lower pre-sealed oil storage region and the lower droplet containing region. There is a transverse micro flow channel (i.e., the second microchannel) with a width of 0.2 mm on the middle partition plate to serve as a channel connecting the lower pre-sealed oil storage region and the lower droplet containing region, and there are recess positioning holes used for ultrasonic bonding on the cross section of the tube wall at positions corresponding to the upper portion of the tubular structure.

Example 2: A Lower Type Microchannel Pre-Sealed Oil Slot Tubular Structure

The lower type microchannel pre-sealed oil slot tubular structure of the sixth embodiment of the disclosure is manufactured through injection molding in the example 2. A material thereof is polypropylene, and a finished product includes several parts made separately, and upper and lower portions of each part are connected to form an integral tubular structure.

Figure 8A:
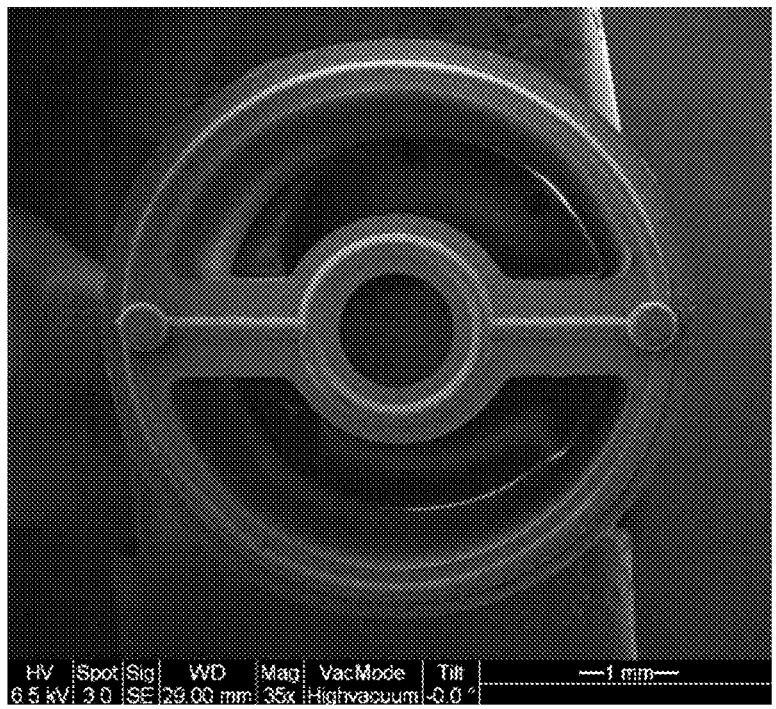
FIG. 8A to FIG. 8D are respectively electron micrographs of a lower surface of an upper portion, an upper surface of a middle portion, a lower surface of the middle portion and an upper surface of a lower portion of a tubular structure of an example 2.
Figure 8B:
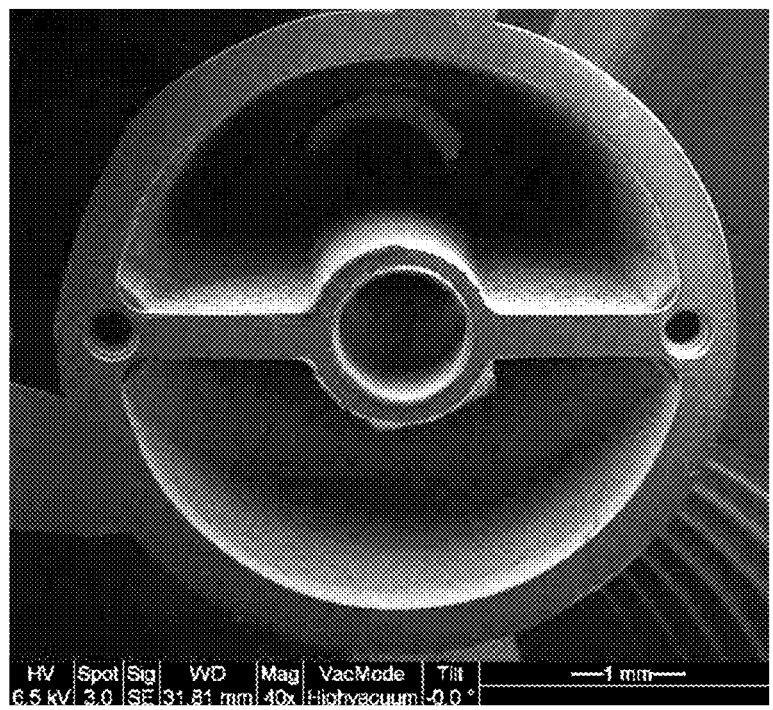
Figure 8C:
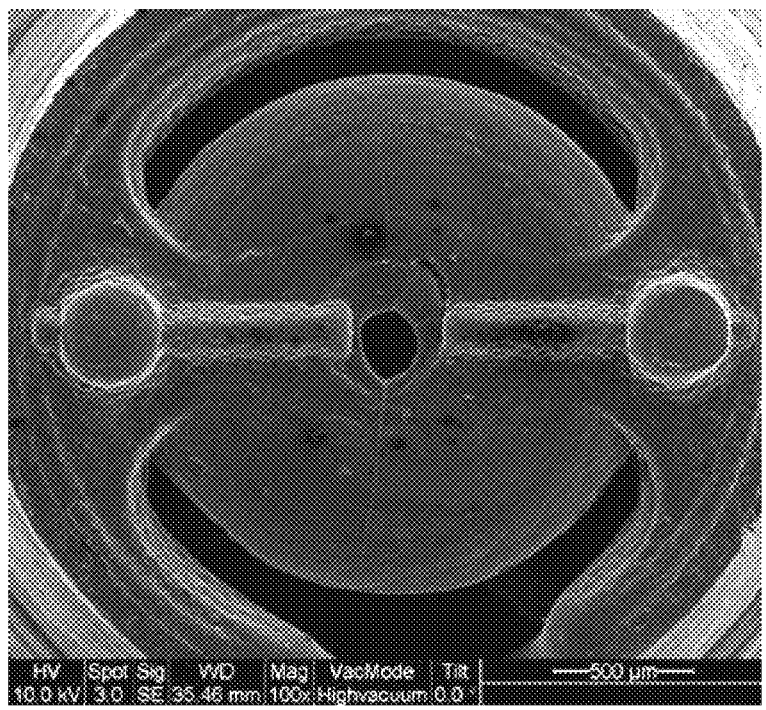
Figure 8D:

FIG. 8A, FIG. 8B, FIG. 8C and FIG. 8D are respectively electron micrographs of a lower surface of an upper portion, an upper surface of a middle portion, a lower surface of the middle portion and an upper surface of a lower portion of the tubular structure of the example 2. Referring to FIG. 8A, the upper portion of the tubular structure has the upper reagent containing region in the middle to partition the upper pre-sealed oil storage region and the upper droplet containing region, and there is an ultrasonic welding structure around the upper reagent containing region, around a cross section of a tube wall and above a cross section of the middle partition plate for bonding the middle portion of the tubular structure, and there are protruding positioning pins on the cross section of the tube wall to facilitate positioning before performing ultrasonic bonding. Referring to FIG. 8B, the middle portion of the tubular structure has the lower reagent containing region in the middle to partition the lower pre-sealed oil storage region and the lower droplet containing region, and there are recess positioning holes used for ultrasonic bonding on the cross section of the tube wall at positions corresponding to the lower surface of the upper portion of the tubular structure. Referring to FIG. 8C, the lower surface of the middle portion of the tubular structure has a middle partition plate to partition the lower pre-sealed oil storage region and the lower droplet containing region, and a through-hole with a diameter of 0.1 mm is formed above the middle partition plate to connect the upper reagent containing region. An ultrasonic welding structure is arranged around the cross region of the tube wall and above the cross section of the middle partition plate to bond the lower portion of the tubular structure, and there are protruding positioning pins on the cross section of the tube wall for positioning before performing ultrasonic bonding. Referring to FIG. 8D, the lower portion of the tubular structure has the middle partition plate to partition the lower pre-sealed oil storage region and the lower droplet containing region, there is a transverse micro flow channel with a width of 0.2 mm on the middle partition plate to serve as a channel connecting the lower pre-sealed oil storage region and the lower droplet containing region, and there are recess positioning holes used for ultrasonic bonding on the cross section of the tube wall at positions corresponding to the lower surface of the middle portion of the tubular structure.

Experimental examples of using the tubular structures of the disclosure to perform ddPCR are described below.

Example 3: Setup of Experimental Equipment

Figure 9:
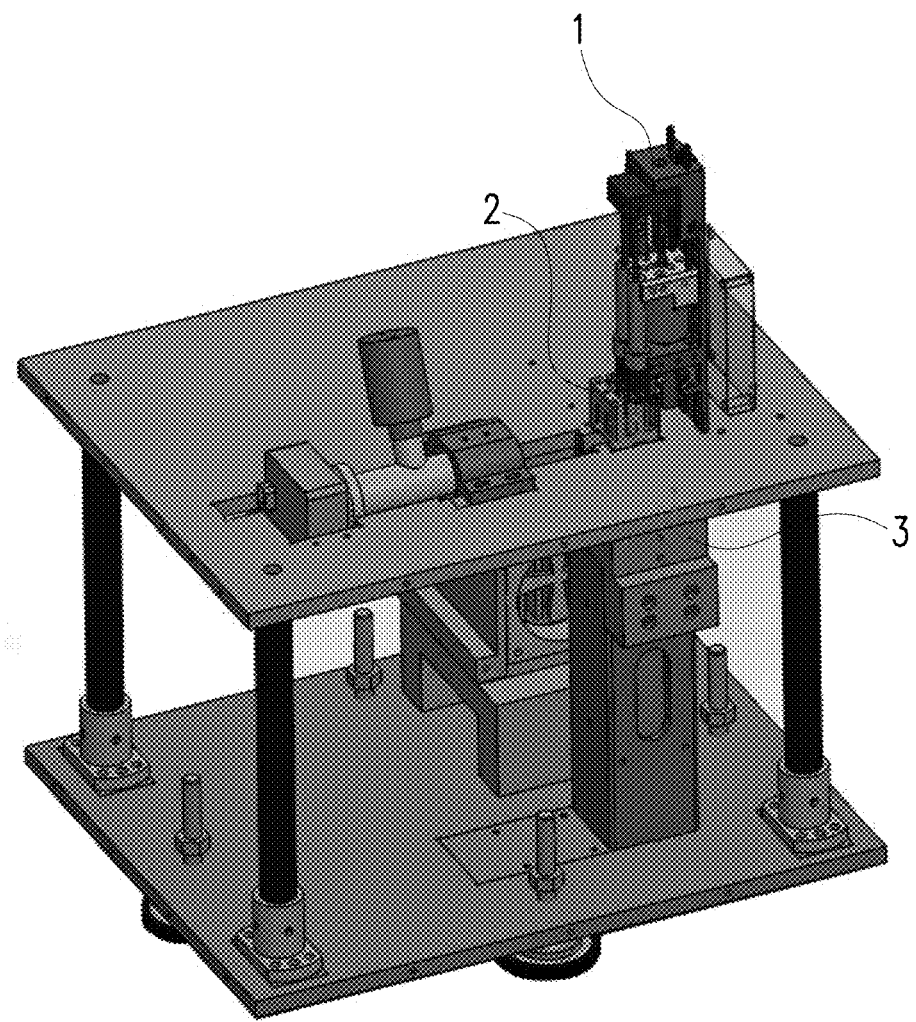
FIG. 9 is a schematic diagram of a ddPCR device of the disclosure.

FIG. 9 is a schematic diagram of a ddPCR device of the disclosure. Referring to FIG. 9, the ddPCR device of the disclosure includes a liquid driving module 1, a cartridge module 2 and detection module 3. The cartridge module 2 includes the tubular structure of the disclosure and a carrier carrying the tubular structure. The liquid driving module 1 includes an injection tube, a motor, a movable component, a fixing mechanism and a position sensing element. The tubular structure of the disclosure is placed inside the carrier, and a heating plate controls rising and falling of a temperature of the carrier. A light transparent window is provided below the tubular structure of the disclosure, and the tubular structure may be detected by the detection module 3 disposed below the carrier. The detection module 3 may include, for example, an optical CCD to record a result of the droplet generation in the tube, or may also include a photomultiplier tube (PMT), which receives optical signals of the droplets, and the optical signals may be recorded and analyzed by a controller.

Example 4: Preparation of the Reagent Solution

The reagent solution used in the example of the disclosure is prepared according to reagent components, concentrations, and volumes shown in a following table 1.

TABLE 1

| Composition | Reagent solution A (L858R Reagent solution) | | Reagent solution B (exon 2 Reagent solution) | | Reagent solution C (λDNA Reagent solution) | |
| --- | --- | --- | --- | --- | --- | --- |
| | Concentration | Volume (μL) | Concentration | Volume (μL) | Concentration | Volume (μL) |
| H2O | | 9.06 | | 3.6 | | 5.98 |
| Master mix | 1 x | 10 | 1 x | 5 | 1 x | 10 |
| F primer | 0.9 μM | 0.18 | | | | |
| R primer | 0.9 μM | 0.18 | | | | |
| probe-mut | 0.2 μM | 0.04 | | | | |
| probe-wt | 0.2 μM | 0.04 | | | | |
| exon 2 F/R/P | | | 3 μM 3 μM 2 μM | 1 | | |
| FIP | | | | | 1.6 μM | 0.32 |
| BIP | | | | | 1.6 μM | 0.32 |
| F3 | | | | | 0.2 μM | 0.04 |
| B3 | | | | | 0.2 μM | 0.04 |
| fluorescent dye SYBR | | | | | 1 x | 0.2 |
| Dye ROX | | | | | 0.25 x | 0.1 |
| DNA | 1 ng/μL | 0.5 | 2 ng/μL | 0.4 | | |
| λDNA | | | | | 0.5 ng/μl | 2 |

Experimental Examples

Experimental Example A: Droplet Generation Test

According to parameters and reagents of a following table 2, the same method as that in the example 1 is used to produce tubular structures with different microchannel sizes, and different flow rates are used to simultaneously push the reagent solutions and the oil agent (droplet generation oil for probes; purchased from Bio-Rad). The generated droplets are collected and are observed by using an optical microscope.

TABLE 2

| Experimental example | A-1 | A-2 | A-3 | A-4 |
| --- | --- | --- | --- | --- |
| Reagent solution | Dyed pure water | Reagent solution A | Reagent solution A | Reagent solution A |
| Diameter of first microchannel (μm) | 300 | 100 | 100 | 100 |
| Diameter of second microchannel (μm) | 500 | 200 | 200 | 200 |

TABLE 2-continued

| Experimental example | A-1 | A-2 | A-3 | A-4 |
| --- | --- | --- | --- | --- |
| Flow rate of reagent solution (μL/min) | 12 | 12 | 6 | 60 |
| Oil agent flow rate (μL/min) | 30 | 30 | 15 | 150 |

Figure 10A:
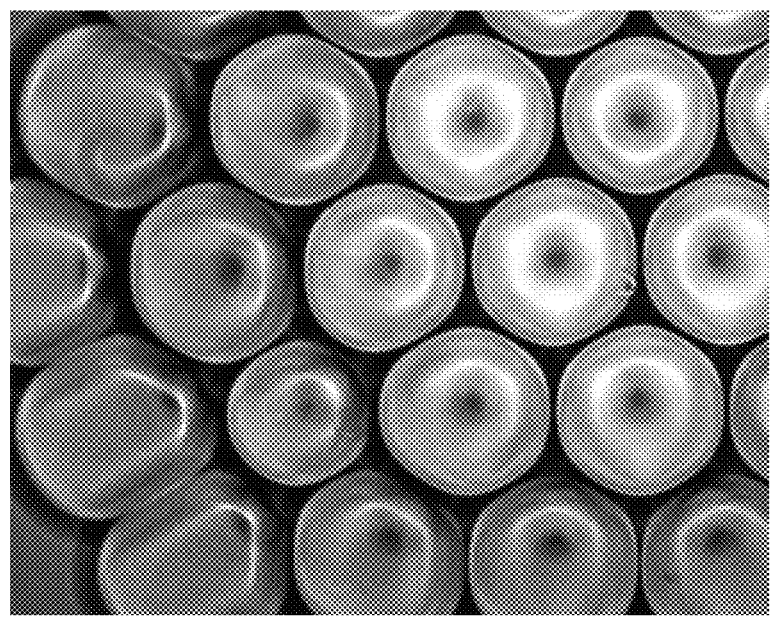
FIG. 10A and FIG. 10B are respectively optical microscope images of droplets of an experimental example A-1 before and after oil films are dried.
Figure 10B:
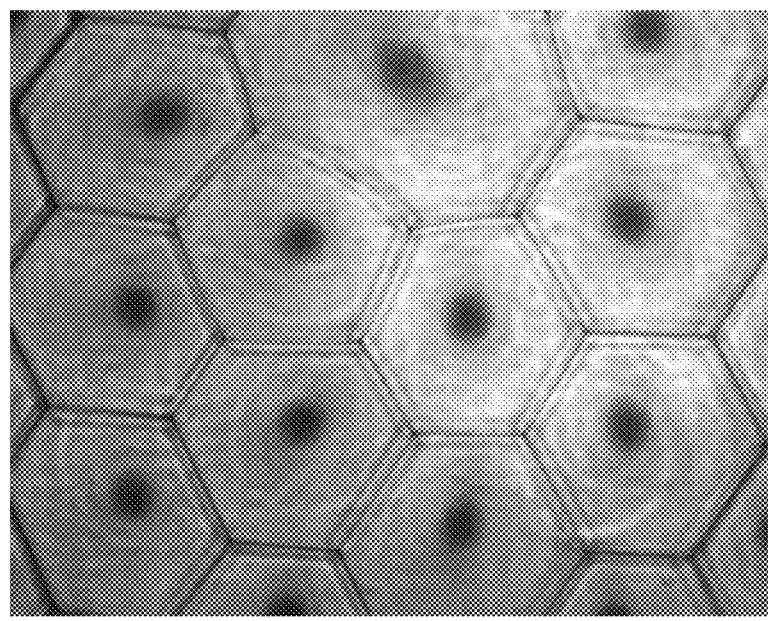
Figure 11A:
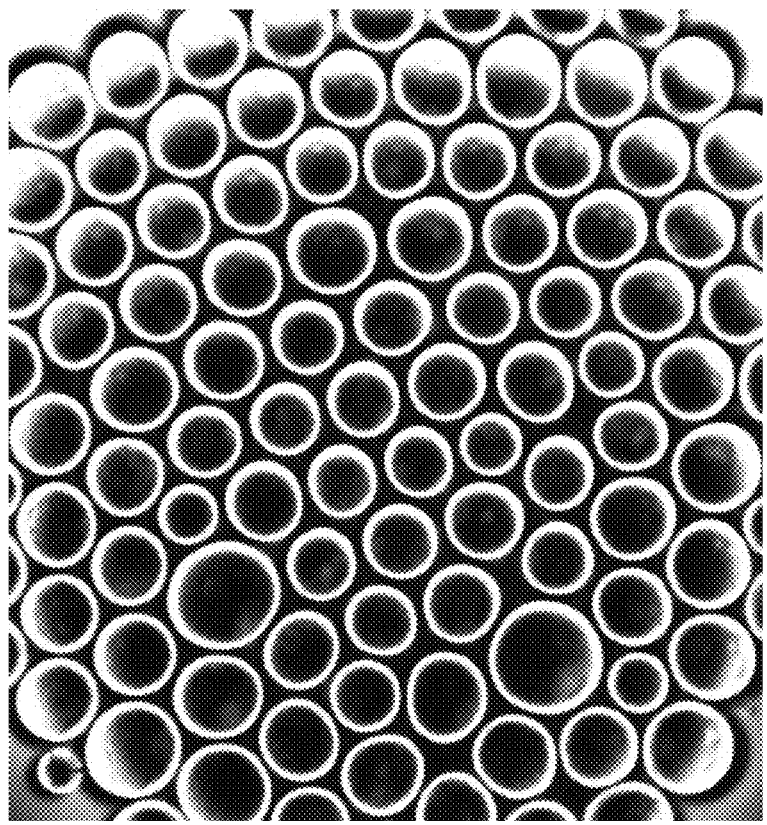
FIG. 11A and FIG. 11B are respectively optical microscope images of droplets of an experimental example A-2 before and after oil films are dried.
Figure 11B:
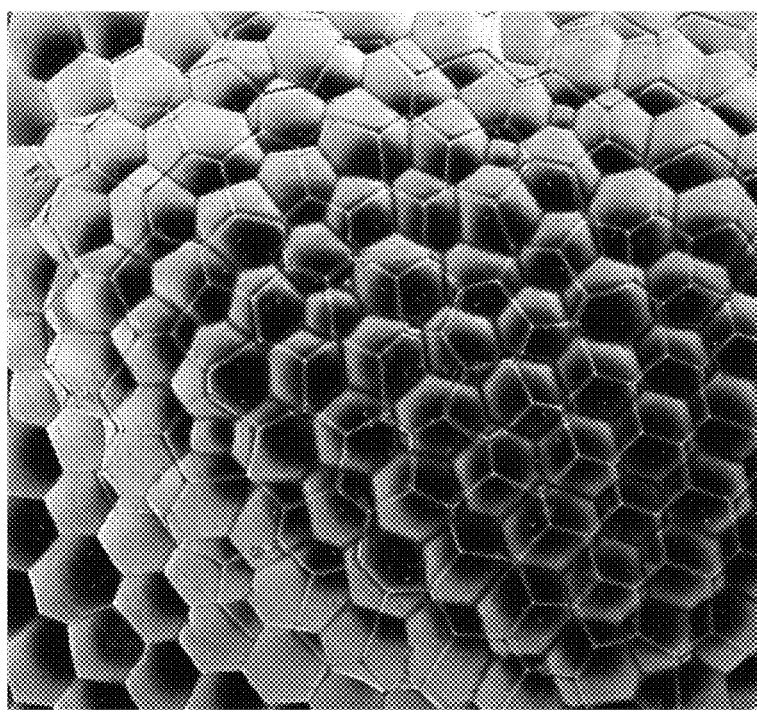
Figure 12:
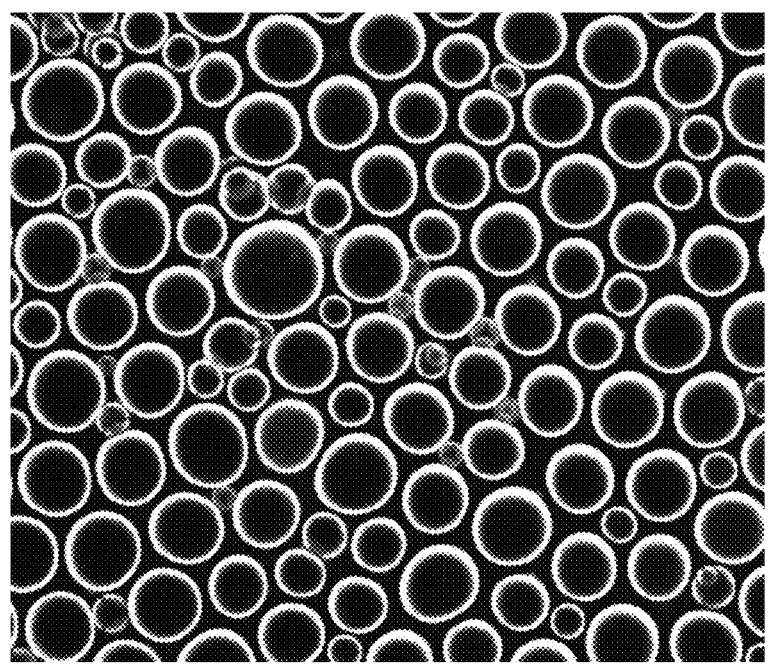
FIG. 12 is an optical microscope image of droplets of an experimental example A-3 before oil films are dried.
Figure 13:
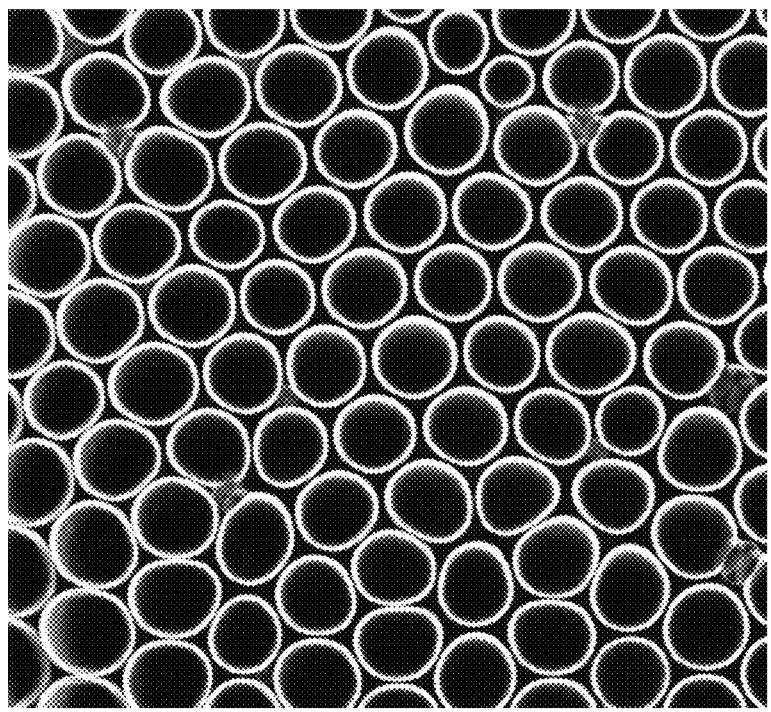
FIG. 13 is an optical microscope image of droplets of an experimental example A-4 before oil films are dried.

FIG. 10A and FIG. 10B are respectively optical microscope images of the droplets of the experimental example A-1 before and after oil films are dried. FIG. 11A and FIG. 11B are respectively optical microscope images of the droplets of the experimental example A-2 before and after oil films are dried. FIG. 12 is an optical microscope image of the droplets of the experimental example A-3 before oil films are dried. FIG. 13 is an optical microscope image of the droplets of the experimental example A-4 before oil films are dried.

In FIG. 10A, it may be observed that the pure water floats in oil. In FIG. 10B, a state that micro droplets are merged may be observed. Comparing the experimental examples A-1 and A-2, it may be clearly observed that under a same operating condition, when a size of the microchannel is reduced, smaller droplets may be obtained. Comparing the experimental examples A-3 and A-4, it may be clearly observed that the slower the flow rate is, the smaller the droplets are obtained; and the faster the flow rate is, the larger the droplets are obtained. In addition, the tubular structures of the disclosure may be used to produce droplets of a uniform size.

Experimental Example B: Setup of a Carrier Module

The carrier module may be used to place the tubular structure of the disclosure and perform temperature control on the droplet region in the tubular structure to perform the PCR. In the following, the carrier modules suitable for the tubular structures of the disclosure are described in more detail by way of examples. However, the carrier modules suitable for the tubular structures of the disclosure are not limited thereto.

Experimental Example B-1: Setup of T-Shaped Heating Carrier Module

Figure 14:
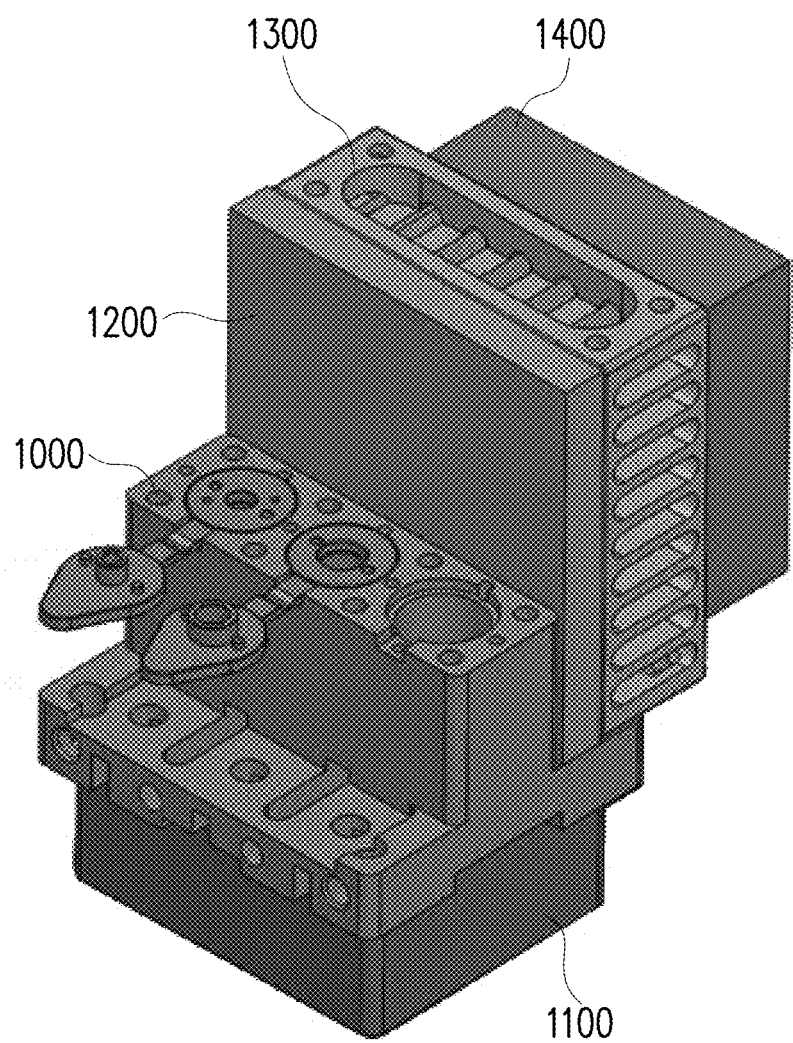
FIG. 14 is a three-dimensional schematic view of a T-shaped heating carrier module of an experimental example B-1.

FIG. 14 is a three-dimensional schematic view of the T-shaped heating carrier module of the experimental example B-1.

Referring to FIG. 14, the T-shaped heating carrier module of the experimental example B-1 has a T-shaped heating carrier 1000 that may hold multiple tubular cartridges at the same time, and a material thereof is aluminum alloy. There is a heat insulation plate 1100 under the heating carrier 1000 to prevent a heat source from entering the machine. A cooling chip 1200 is arranged on a side of the heating carrier 1000 to provide a temperature controller required for heating and cooling cycles. The cooling chip 1200 is disposed on a cooling copper plate 1300, and the cooling copper plate 1300 has a fin design with a cooling function in internal. One side of the cooling copper plate 1300 is connected to a cooling fan 1400, and the cooling fan 1400 may export a heat source generated by the cooling chip 1200.

Experimental Example B-2: Setup of Single-Plane Thin Shell Plate Heating Carrier Module FIG. 15 is a three-dimensional schematic view of the single-plane thin shell plate heating carrier module of the experimental example B-2.

Figure 15:
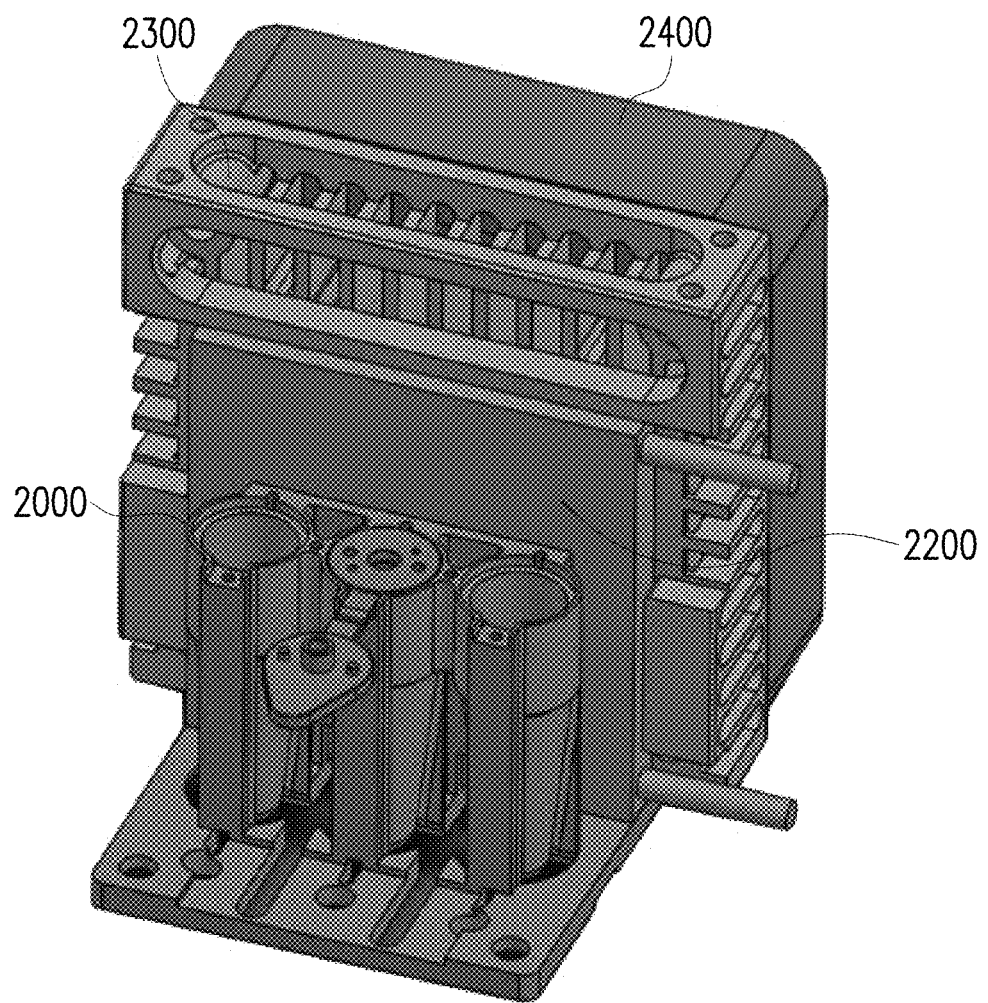
FIG. 15 is a three-dimensional schematic view of a single-plane thin shell plate heating carrier module of an experimental example B-2.

Referring to FIG. 15, the single-plane thin shell plate heating carrier module of the experimental example B-2 has a single-plane thin shell plate heating carrier 2000 that may hold multiple tubular cartridges at the same time, a material thereof is aluminum alloy, and a surface thereof is anodized. A thickness of a structural entity of the thin shell plate heating carrier 2000 is reduced to reduce a heat loss of metal during a temperature control cycle, and a heat insulation plate (not shown) may be provided below the heating carrier 2000 to prevent a heat source from entering the machine. A side plane of the heating carrier 2000 is connected to a cooling chip 2200. The cooling chip 2200 provides a temperature controller required by heating and cooling cycles. The cooling chip 2200 is placed on a cooling copper plate 2300, and the cooling copper plate 2300 has a fin design with a cooling function in internal. One side of the cooling copper plate 2300 is connected to a cooling fan 2400, and the cooling fan 2400 may export a heat source generated by the cooling chip 2200.

Experimental Example B-3: Setup of Single-Plane Sleeve-Type Heating Carrier Module FIG. 16 is a three-dimensional schematic view of the single-plane sleeve-type heating carrier module of the experimental example B-3.

Figure 16:
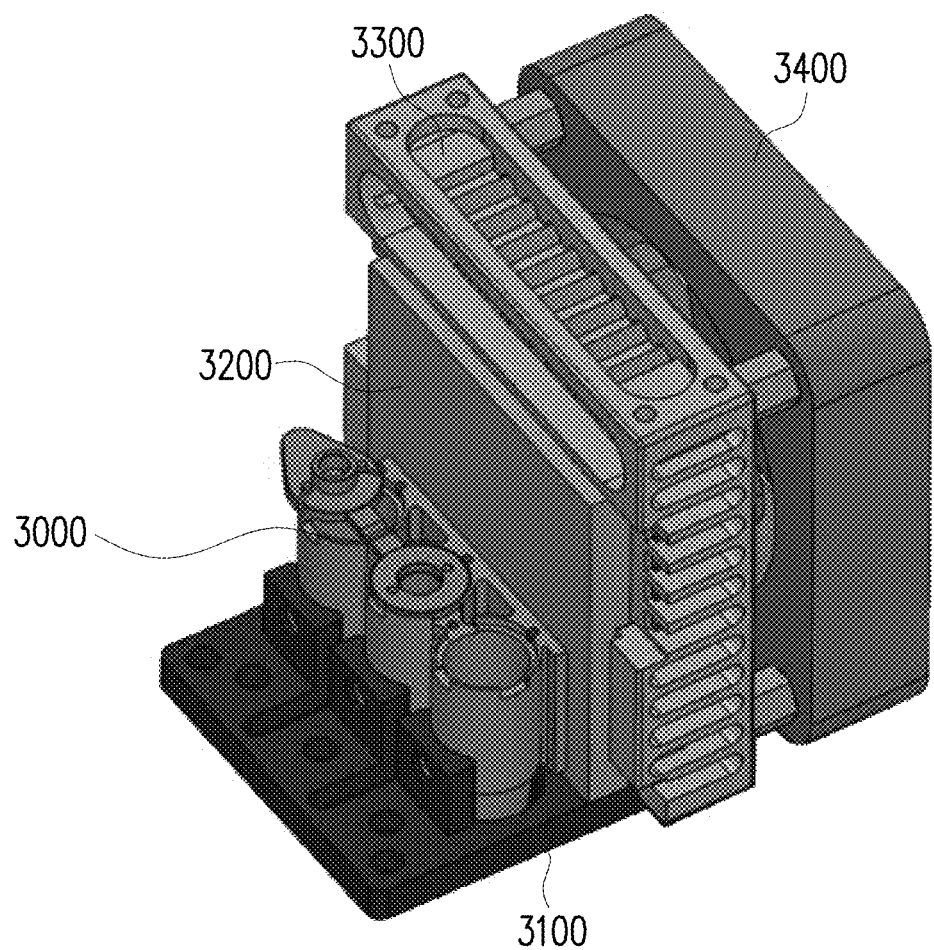
FIG. 16 is a three-dimensional schematic view of a single-plane sleeve-type heating carrier module of an experimental example B-3.

Referring to FIG. 16, the single-plane sleeve-type heating carrier module of the experimental example B-3 has a single-plane sleeve-type heating carrier 3000 that may hold multiple tubular cartridges at the same time, a material thereof is aluminum alloy, and a surface thereof is anodized. The tubular cartridges are tightly placed inside the sleeve-type heating carrier 3000, the tubes thereof are isolated by air to form independent structures, and a metal material part is extremely simplified to reduce a heat loss of metal during the temperature control cycle. A carrier plate 3100 under the sleeve-type heating carrier 3000 is another heat insulation material, which may prevent the heat source from entering the machine. A side plane of the heating carrier 3000 is connected to a cooling chip 3200. The cooling chip 3200 provides a temperature controller required for heating and cooling cycles. The cooling chip 3200 is placed on a cooling copper plate 3300, and a heat conductive paste is coated on a plane of the cooling chip 3200 contacting the cooling copper plate 3300 to increase a heat conduction effect. The cooling copper plate 3300 has a fin design with a cooling function in internal. One side of the cooling copper plate 3300 is connected to a cooling fan 3400, and the cooling fan 3400 may export a heat source generated by the cooling chip 3200.

Experimental Example B-4: Setup of Multi-Tube Single-Side Flat-Edge Type Heating Carrier Module FIG. 17 is a three-dimensional schematic view of the multi-tube single-side flat-edge type heating carrier module of the experimental example B-4.

Figure 17:
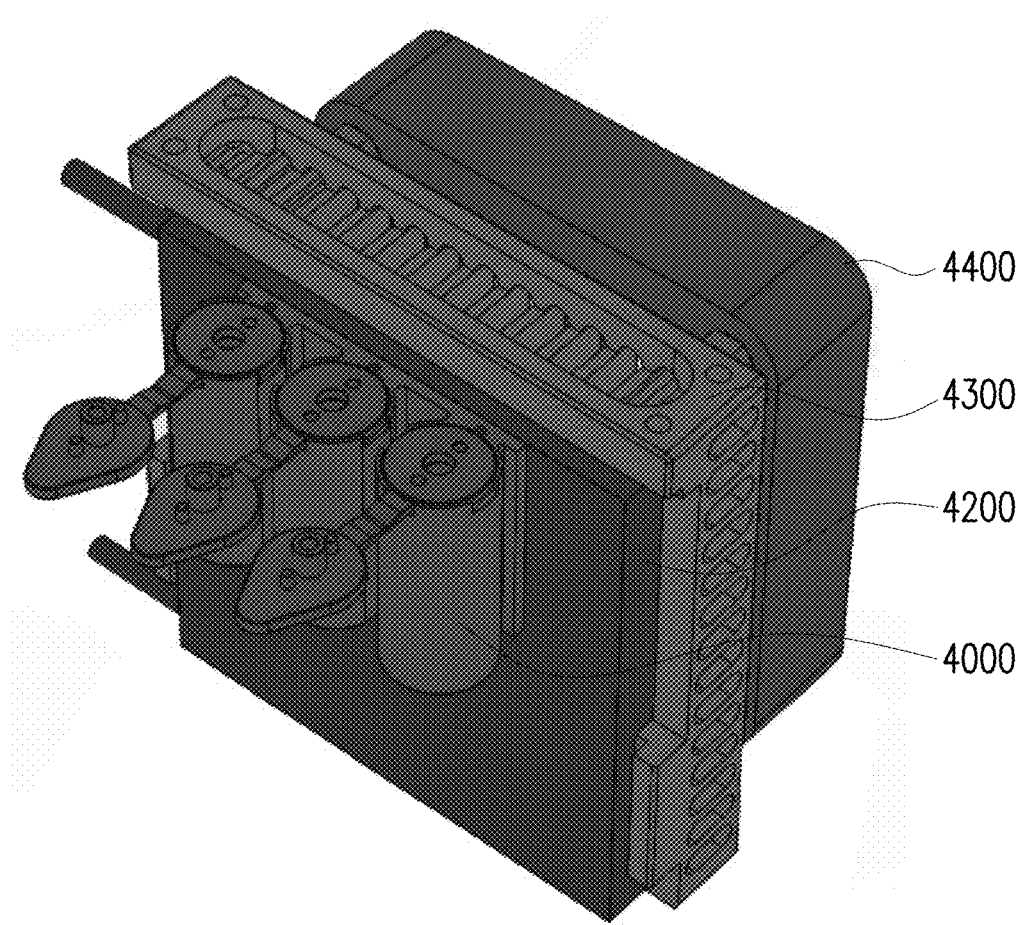
FIG. 17 is a three-dimensional schematic view of a multi-tube single-side flat-edge type heating carrier module of an experimental example B-4.

Referring to FIG. 17, the multi-tube single-side flat-edge type heating carrier module of the experimental example B-4 has a multi-tube single-side flat-edge type heating carrier 4000 that may hold multiple tubular cartridges at the same time, and a material thereof is aluminum alloy. A side of the multi-tube single-side flat-edge type heating carrier 4000 is a plane, which is attached with a cooling chip 4200 to provide a temperature controller required for heating and cooling cycles. There is a gap between each two adjacent tubes of the heating carrier 4000 to isolate a heat transfer effect between different tubes and maintain a uniform temperature state among the tubes. The cooling chip 4200 is placed on a cooling copper plate 4300, and the cooling copper plate 4300 has a fin design with a cooling function in internal. One side of the cooling copper plate 4300 is connected to a cooling fan 4400, and the cooling fan 4400 may export a heat source generated by the cooling chip 4200.

Experimental Example C: Temperature Cycle Test

In the experiment example C, the heating carrier modules of the experimental example B-1, the experimental example B-2, the experimental example B-3, and the experimental example B-4 are respectively applied to perform temperature cycle tests to compare temperature control effects of the different heating carrier modules.

Experimental Example C-1: Test a Temperature Control Effect of the T-Shaped Heating Carrier Module of the Experimental Example B-1

A general commercial PCR tube (purchased from Axygen; model No. PCR-02-C) and a tubular structure of the example 1 are respectively placed inside the carrier. 200 μL of oil (CAS No. 8042-47-5; purchased from Tedia) is filled in the PCR tube. 30 μL of oil is respectively filled in the middle and an outer side of the tubular structure of the example 1. Platinum temperature sensors are inserted into each slot in the PCR tube and the tubular structure of the example 1, and a temperature of each sensing position is recorded by a memory-type four-window thermometer (TM-947SD) to compare temperature variation curves of each of the sensing points varied along with time under a same temperature control condition.

Figure 18:
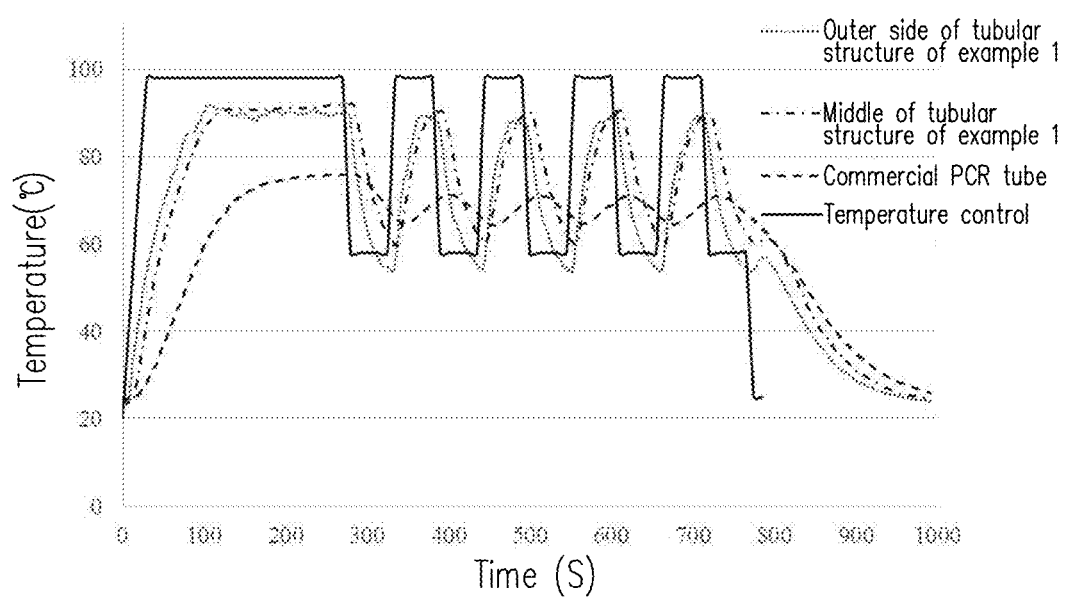
FIG. 18 is a diagram illustrating temperature variation curves of an experimental example C-1.

FIG. 18 is a diagram illustrating the temperature variation curves of the experimental example C-1. Cycle temperature control is set between 98° C. and 58° C. A temperature response in the PCR tube is the slowest due to that a volume of liquid in the PCR tube is the largest, so that a response rate for heating and cooling is slow, and a provided heat source cannot reach a set temperature range. In the tubular structure of the example 1, since a volume of the oil is relatively less, a heating and cooling variation rate of the oil in the tube is significantly higher than a measurement result of the temperature in the PCR tube, wherein the heating and cooling variation rate is better near the heating source.

The design of the T-shaped heating carrier has an effect of double-sided heating, but the large volume of metal reduces the response rate of heating and cooling. Taking a temperature variation in a side slot of the tubular structure as an example, it takes 59 seconds for heating from 30° C. to 80° C., and a heating rate is about 0.85° C./sec; and it takes 28 seconds for cooling from 90° C. to 60° C., and a cooling rate is about 1.1° C./sec.

Experimental Example C-2: Test a Temperature Control Effect of the Single-Plane Thin Shell Plate Heating Carrier Module of the Experimental Example B-2

The single-plane thin shell plate heating carrier module of the experimental example B-2 is used to perform the temperature cycle test. Three tubular structures of the example 1 are placed inside the carrier, and 30 µL of oil (CAS No. 8042-47-5; purchased from Tedia) is respectively filled in an inner side and the outer side of the tubular structures of the example 1, and platinum temperature sensors are inserted into each slot inside the tubes, and a temperature of each sensing position is recorded by a memory-type four-window thermometer (TM-947SD) to compare temperature variation curves of each of the sensing points varied along with time under a same cycle temperature control condition.

Figure 19:
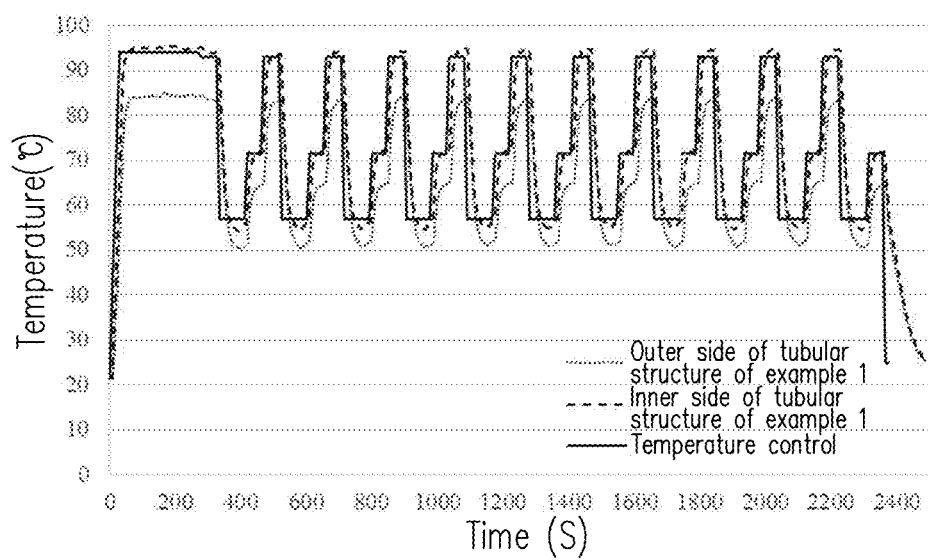
FIG. 19 is a diagram illustrating temperature variation curves of an experimental example C-2.

FIG. 19 is a diagram illustrating the temperature variation curves of the experimental example C-2. Cycle temperature control points are respectively set to 93° C., 57° C., and 71.5° C., a temperature sensor for feedback control is placed in an outer hole of the heating carrier, and the temperature sensors respectively measure temperatures of the oil in inner and outer side slots of the tubular structures. Since the inner side of the tubular structure is tightly close to the heating source, a heating and cooling variation rate of the oil in the tube is significantly higher than a measurement result of the temperature of the outer side of the tubular structure.

In the single-plane thin shell plate heating carrier of the experimental example B-2, since a metal volume of the carrier is reduced, the response rate of heating and cooling is greatly improved when the same temperature control equipment is used. Taking a temperature variation in the inner side slot of the tubular structure as an example, it takes 24 seconds for heating from 30° C. to 80° C., and the heating rate is about 2.1° C./sec; and it takes 21 seconds for cooling from 90° C. to 60° C., and the cooling rate is about 1.4° C./sec. The single-plane thin shell plate heating carrier of the experimental example B-2 may implement more effective temperature control on the tubular structures of the disclosure.

Experimental Example C-3: Test a Temperature Control Effect of the Single-Plane Sleeve-Type Heating Carrier Module of the Experimental Example B-3

The single-plane sleeve-type heating carrier module of the experimental example B-3 is used to perform the temperature cycle test. A single tubular structure of the example 1 is placed in the middle inside the carrier, and 30 µL of oil (CAS No. 8042-47-5; purchased from Tedia) is respectively filled in the inner side, the middle, and the outer side of the tubular structure of the example 1, and platinum temperature sensors are inserted into each slot inside the tube, and a temperature of each sensing position is recorded by a memory-type four-window thermometer (TM-947SD).

Cycle temperature control points are respectively set to 93° C., 57° C., and 71.5° C., a temperature sensor for feedback control is placed in a middle hole of the heating carrier, and the temperature sensors respectively measure temperatures of the oil in the inner side, middle, and outer side slots of the tubular structure to compare temperature variation curves of each of the sensing points varied along with time in a same cycle.

Figure 20:
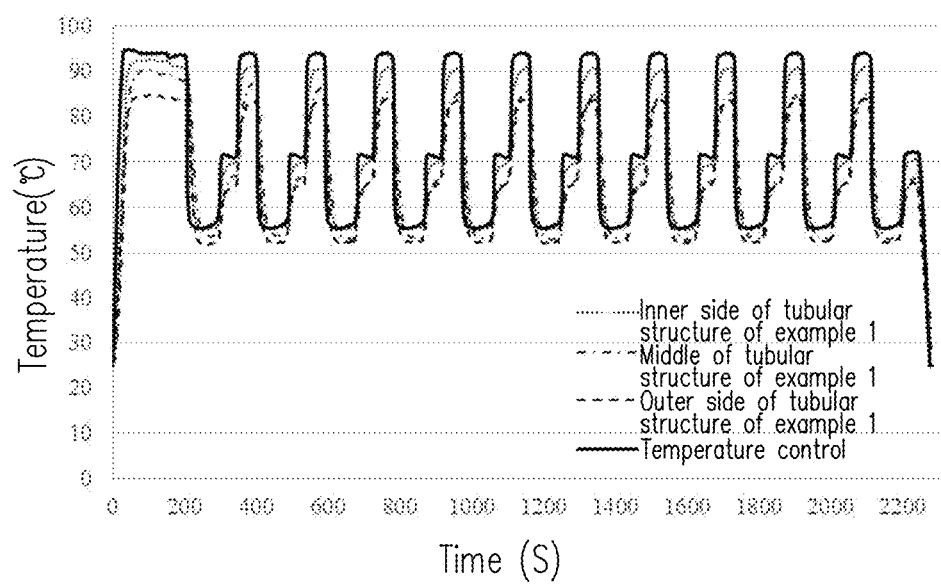
FIG. 20 is a diagram illustrating temperature variation curves of an experimental example C-3.

FIG. 20 is a diagram illustrating the temperature variation curves of the experimental example C-3. It takes 26 seconds for heating the inner side slot from 30° C. to 80° C., and the heating rate is about 1.92° C./sec; and it takes 17 seconds for cooling from 90° C. to 60° C., and the cooling rate is about 1.76° C./sec. The temperature variation rate in the inner side slot achieved by the single-plane sleeve-type heating carrier module of the experimental example B-3 reaches a same level as the single-plane thin shell plate heating carrier module of the experimental example B-2. Moreover, the temperature in the outer side slot also has a significant improving effect, and the heating and cooling variation rates of each slot are more consistent, which has a smaller difference with a temperature setting value, so that the single-plane sleeve-type heating carrier module of the experimental example B-3 is especially suitable for serving as a heating carrier of the temperature control cycle.

Experimental Example C-4: Temperature Cycle Test of the Multi-Tube Single-Side Flat-Edge Type Heating Carrier Module of the Experimental Example B-4

The multi-tube single-side flat-edge type heating carrier module of the experimental example B-4 is applied to perform the temperature cycle test. The carrier is wrapped by a heat insulation material, and three PCR tubes (purchased from Axygen; model No. PCR-02-C) are placed inside the carrier, and 20 µL of mineral oil (CAS No. 8042-47-5; purchased from Tedia) and 10 µL of the reagent solution B are filled in the PCR tubes. A platinum temperature sensor is inserted into an inner slot of each of the PCR tubes, and a temperature of each sensing position is recorded by a memory-type four-window thermometer (TM-947SD).

Figure 21:
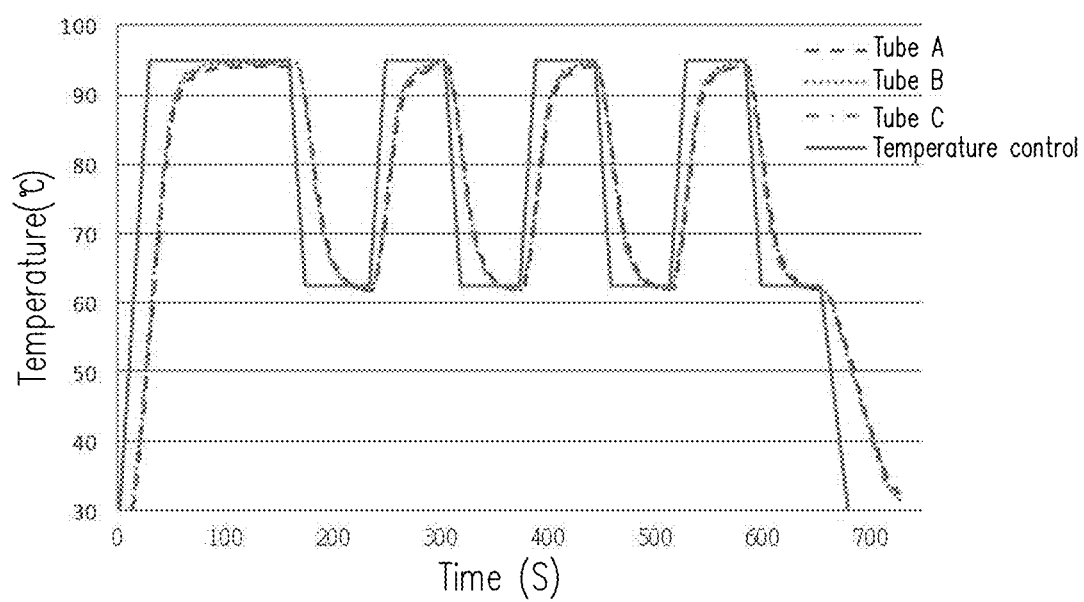
FIG. 21 is a diagram illustrating temperature variation curves of an experimental example C-4.

FIG. 21 is a diagram illustrating temperature variation curves of the experimental example C-4. The cycle temperature control is set between 95° C. and 62.5° C., and a temperature measurement result shows that cycle temperature variation curves in the PCR tubes tend to be consistent and reach a temperature stable balance region, and a temperature error amount the tubes is <0.5° C. By comparing a setting curve of the cycle temperature control with temperature measurement values of the temperatures in the PCR tubes, it is known that a temperature response in each of the PCR tubes is slow, since the heat is transferred from a heating plate to the heating carrier and is then transferred from the heating carrier to the inside of the tube, so that a heating and cooling response rate is slower, and it takes a longer time to reach a stable temperature.

Experimental Example C-5: Compare Cycle Temperature Control Effects of the Commercial PCR Tube and the Tubular Structures of the Disclosure In the experimental example C-5, the cycle temperature control effects of the commercial PCR tube and the tubular structures of the disclosure are compared. Three commercial PCR tubes (purchased from Axygen; model No. PCR-02-C) and three tubular structures of the example 1 are respectively placed inside two multi-tube single-side flat-edge type heating carriers of the experimental example B-4. The commercial PCR tubes and the tubular structures according to the disclosure are respectively filled with 20 µL of the mineral oil (CAS No. 8042-47-5; purchased from Tedia) and 10 µL of the reagent solution B. A platinum temperature sensor is inserted into an inner slot of a middle tube, and a temperature of each sensing position is recorded by a memory-type four-window thermometer (TM-947SD), and temperature variation curves of each of the sensing points varied along with time are compared under the same temperature control condition.

Figure 22:
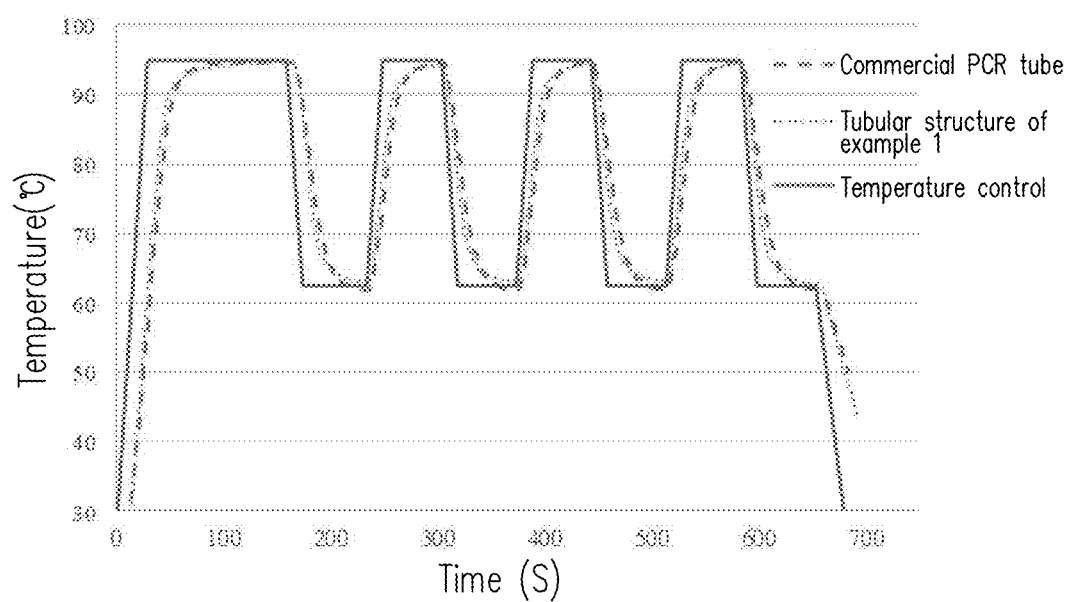
FIG. 22 is a diagram illustrating temperature variation curves of an experimental example C-5.

FIG. 22 is a diagram illustrating the temperature variation curves of the experimental example C-5. An experimental cycle temperature result shows that the liquid in a side slot of the tubular structure of the example 1 has faster heating and cooling rates. Since a distribution space of the liquid in the side slot of the tubular structure of the example 1 is a thin-wall half-ring shape, it avails improving a response rate in rising and falling of the cycle temperature compared with a spherical distribution of the liquid at the bottom in the general commercial PCR tube.

Experimental Example C-6: Compare Effects of Different Materials of Cooling Plate on PCR Cycle Temperature In the experimental example C-6, effects of different materials of the cooling plate on the PCR cycle temperature are compared. A function of the cooling plate is to export and distribute the heat generated by the cooling chip to the cooling plate, and then expel it into the air by a fan. Namely, one side of the cooling chip is the heating carrier, and another side is the cooling plate. In case that other experimental conditions are fixed, brass and aluminum alloy are respectively used to produce the cooling plate. The multi-tube single-side flat-edge type heating carrier of the experimental example B-4 is used to perform the temperature cycle test. A commercial PCR tube is placed inside the heating carrier, and 20 µL of the mineral oil (CAS No. 8042-47-5; purchased from Tedia) and 10 µL of the reagent solution B are filled in the commercial PCR tube. A platinum temperature sensors is inserted into an inner slot of each of the tubes, and a temperature of each sensing position is recorded by a memory-type four-window thermometer (TM-947SD), and temperature variation curves of each of the sensing points varied along with time are compared under the same temperature control condition.

Figure 23:
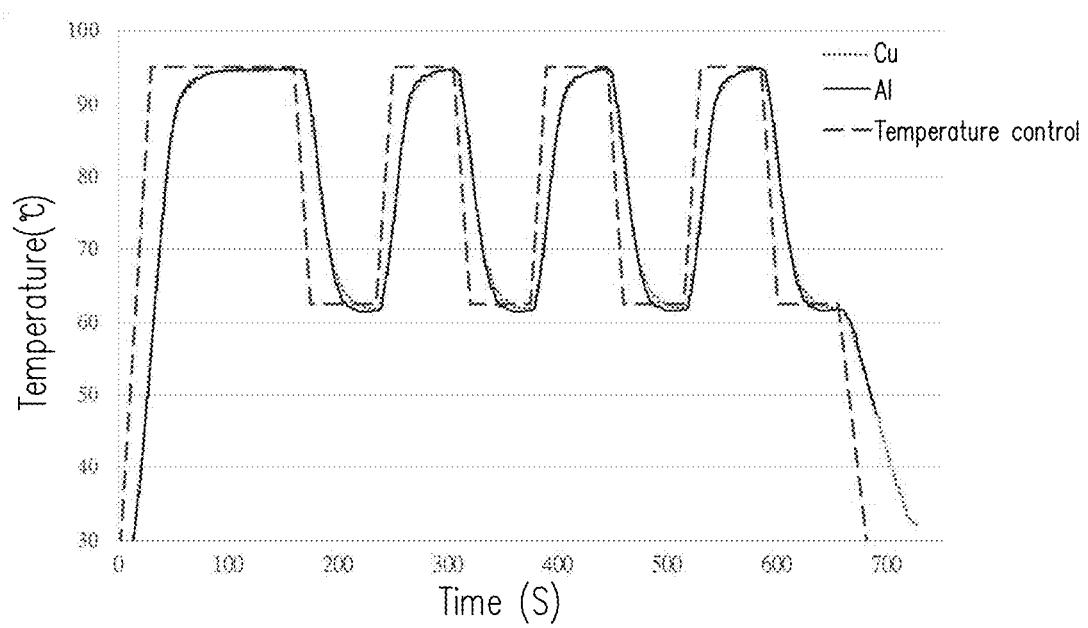
FIG. 23 is a diagram illustrating temperature variation curves of an experimental example C-6.

FIG. 23 is a diagram illustrating the temperature variation curves of the experimental example C-6. An experimental result shows that the material of the cooling plate has no significant effect on the temperature rising and falling rate of the liquid in the tube. Therefore, although pure copper has higher thermal conductivity than pure aluminum, copper alloys have a disadvantage of larger weight per unit volume, while aluminum alloys are cheap, have low density, are easy for processing and molding, etc., and are widely used in heat sink products of CPU. When there is no significant difference in a heat dissipation performance, to use aluminum alloy to produce the cooling plate has higher economic benefits.

Experimental Example D: Polymerase Chain Reaction (PCR)

Experimental Example D-1: Compare Results of Performing PCR by Using the Experimental Equipment of the Disclosure and Commercial PCR Instrument In the experimental example D-1, the tubular structure of the example 1 and the single-plane sleeve-type heating carrier module of the experimental example B-3 of the disclosure are used to perform the PCR test, and a test result thereof is compared with a result obtained by using the commercial PCR instrument to perform the PCR test. The experimental example adopts a loop mediated isothermal amplification (LAMP) method to perform the test. The commercial PCR instrument is a multi-fluorescent gene quantitative spectrometer (Applied Biosystems Inc., 7500, Real time PCR). After the PCR is ended, agarose gel electrophoresis is applied to detect a result of the PCR, so as to compare the results of performing the PCR test by using the experimental equipment of the disclosure and using the commercial PCR instrument in parallel comparison.

First, 20 µL of the reagent solution C and 20 µL of oil (CAS No. 8042-47-5; purchased from Tedia) are respectively added to the reagent containing region and the oil slot of the tubular structure of the example 1. The single-plane sleeve-type heating carrier module of the experimental example B-3 is used to respectively perform constant temperature PCR tests of constant temperatures of 66.5° C. and 65° C. for holding 90 minutes on the tubular structure. Moreover, the multi-fluorescent gene quantitative spectrometer is used to perform PCR amplification at an operating temperature of 65° C. by using the same reagent. Then, the agarose gel electrophoresis is applied to interpret a DNA amplification signal.

Figure 24:
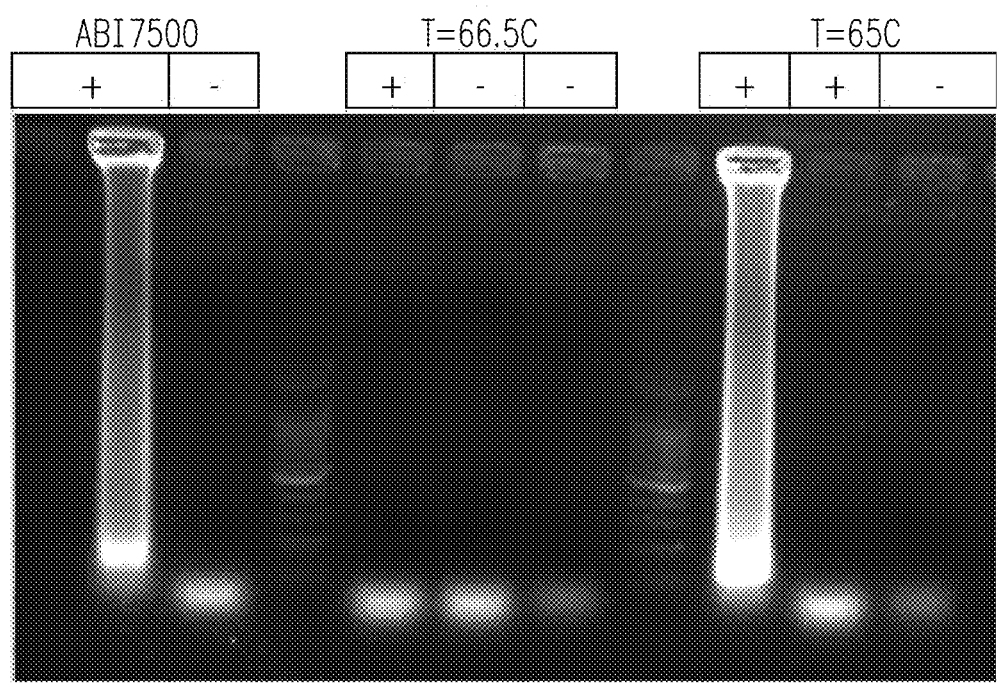
FIG. 24 is a picture of using agarose gel electrophoresis to interpret a DNA amplification signal after using an ABI 7500 and experimental equipment of the disclosure to perform PCR.

FIG. 24 is a picture of using the agarose gel electrophoresis to interpret the λDNA amplification signal after using the ABI 7500 and the experimental equipment of the disclosure to perform the PCR. A left part of FIG. 24 shows an amplification result of DNA generated by an ABI 7500 instrument platform, and positive signals have high brightness and are significantly different from negative signals. A middle part is a DNA Ladder, which has DNA segments of different lengths to serve as a reference for DNA molecular weight analysis. A right part of FIG. 24 is a result of performing the constant temperature PCR by using the single-plane sleeve-type heating carrier of the disclosure. The result shows that when the constant temperature is 66.5° C., neither positive nor negative signal has a signal amplification result. When the constant temperature is 65° C., the positive and negative signals may all produce a correct result. From the result of the experimental example, it may be observed that by using the tubular structure and the heating carrier of the disclosure under proper reaction conditions, the PCR may be effectively performed to obtain the correct result.

Experimental Example D-2: PCR Test of Commercial PCR Tube

In the experimental example D-2, three commercial PCR tubes (purchased from Axygen; model No. PCR-02-C) are placed in the multi-tube single-side flat-edge type heating carrier of the experimental example B-4 equipped with a temperature control device to perform a PCR experiment. After the PCR experiment is completed, the agarose gel electrophoresis is applied to perform parallel comparison after the DNA amplification.

First, 10 μL of the PCR reagent solution B and 20 μL of oil (CAS No. 8042-47-5; purchased from Tedia) are filled in the commercial PCR tubes, and a cycle temperature test is performed after sealing. In the multi-tube single-side flat-edge type heating carrier module of the experimental example B-4, the temperature is first raised to 95° C. and held for 10 minutes, and then a double-temperature layer multiple thermal cycle experiment is performed to carry out a DNA amplification experiment test. Fixed parameters of the experiment are a high temperature of 95° C. and a low temperature of 62.5° C., and operating control parameters are respectively a high temperature holding time, a low temperature holding time and a number of times of the thermal cycles. A control parameter test of the DNA amplification is performed, and a result thereof is shown in FIG. 25 and a following table 3.

Figure 25:
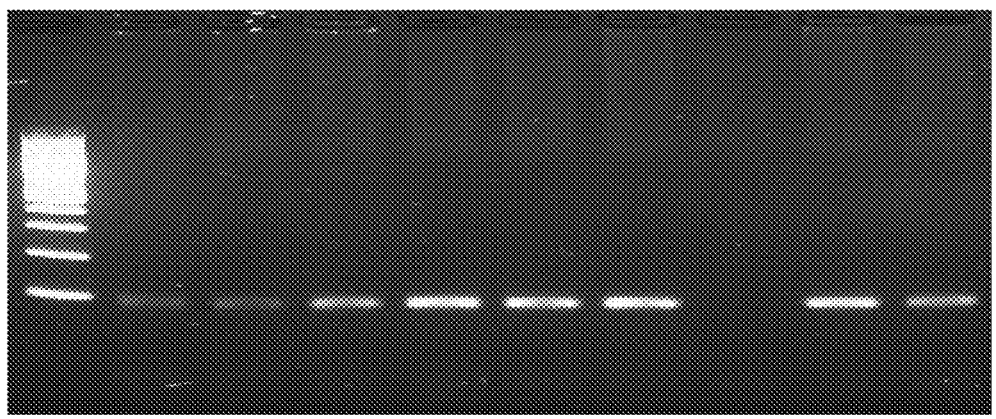
FIG. 25 is a picture of an experimental result of agarose gel electrophoresis of a PCR experiment of an experimental example D-2.

FIG. 25 is a picture of an experimental result of agarose gel electrophoresis of the PCR experiment of the experimental example D-2. A leftmost column of FIG. 25 is a DNA Ladder, which has DNA segments of different lengths to serve as a reference for DNA molecular weight analysis. Columns 2-4 of FIG. 25 are results of DNA amplification signals generated in different tubes under the same thermal cycling operating conditions, wherein the positive signals of each tube are all correct, and the results show that after the thermal cycling experiment process, the DNA is amplified at a correct position, and repeatability between each tube is good. In columns 5-7 of FIG. 25, the high temperature holding time is shortened to 10 seconds, and other experimental conditions are fixed, and the result of agarose gel electrophoresis shows that intensities of the DNA amplification signals increase, and the high-intensity amplification signals are maintained between the tubes. In columns 8-10 of FIG. 25, the experimental conditions the first time are maintained, the number of times of the thermal cycles is increased, and a negative sample is placed for comparison. The result of agarose gel electrophoresis shows that the intensities of the DNA amplification signals are all increased compared to the operating conditions of the first time, and positive and negative signals may all produce correct results.

The experimental results show that by using the multi-tube single-side flat-edge type heating carrier of the experimental example B-4 equipped with the temperature control device and using the commercial PCR tube to perform the DNA amplification test, the result of DNA signal amplification may be achieved under controlled operating conditions.

TABLE 3

| Column | 2 | 3 | 4 | 5 | 6 | 7 | 8 | 9 | 10 |
|---|---|---|---|---|---|---|---|---|---|
| High temperature | 95° C.-20 s | | | 95° C.-10 s | | | 95° C.-20 s | | |
| Low temperature | 62.5° C.-40 s | | | 62.5° C.-40 s | | | 62.5° C.-40 s | | |
| Cycle | 35 times | | | 35 times | | | 40 times | | |
| P/N | P | P | P | P | P | P | N | P | P |

Experimental Example D-3: PCR Test of Using the Tubular Structure of the Example 1

In the experimental Example D-3, three tubular structures of the example 1 are placed in the multi-tube single-side flat-edge type heating carrier of the experimental example B-4 equipped with the temperature control device for PCR experiment. Meanwhile, a 96-well PCR thermal cycler (Applied Biosystems Inc., Veriti) is used to perform a reagent verification test, and agarose gel electrophoresis is applied to perform parallel comparison after DNA amplification.

First, 20 μL of the PCR reagent solution B and 20 μL of oil (CAS No. 8042-47-5; purchased from Tedia) are filled in the inner side slot of the tubular structure of the example 1, and the cycle temperature test is performed after sealing. In the multi-tube single-side flat-edge type heating carrier module of the experimental example B-4, the temperature cycle test is performed for 35 times between two set temperatures of a high temperature of 95° C. and a low temperature of 62.5° C. Moreover, a commercial 96-well PCR thermal cycler (Applied Biosystems Inc., Veriti) is used to perform the verification test, and a same reagent is applied to perform parallel comparison. The results are shown in FIG. 26 and a following table 4.

TABLE 4

| Column | 2 | 3 | 4 | 5 | 6 | 7 |
|---|---|---|---|---|---|---|
| Platform | Veriti | | | | Example B-4 | |
| High temperature | 95° C.-20 s | | | | 95° C.-30 s | |
| Low temperature | 63° C.-45 s | | | | 62.5° C.-40 s | |
| Cycle | 35 times | | | | 35 times | |
| P/N | P | N | P | N | N | P |

Figure 26:
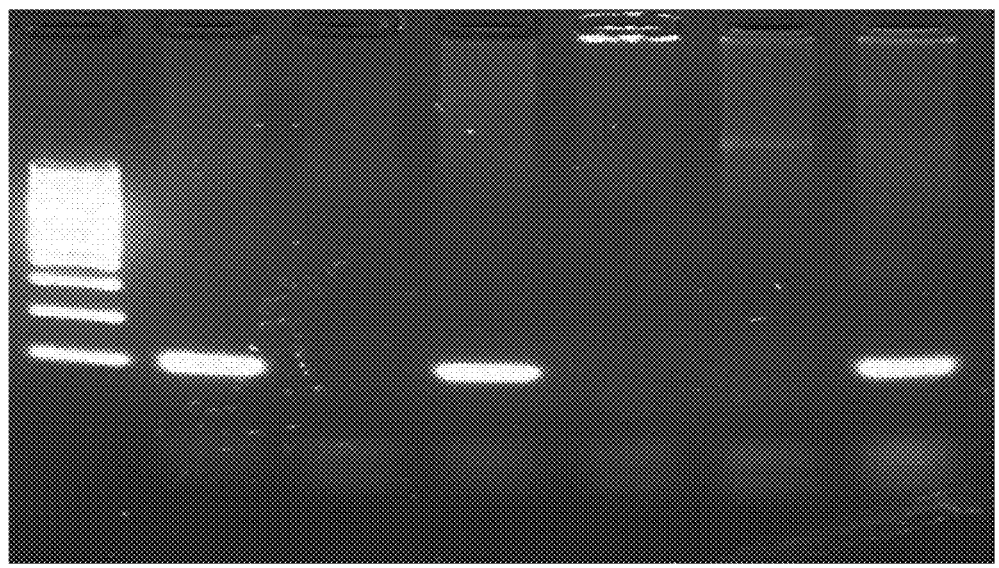
FIG. 26 is a picture of an experiment result of agarose gel electrophoresis of a PCR experiment of an experimental example D-3.

In this experiment, agarose gel electrophoresis is applied to interpret the DNA amplification signal, FIG. 26 is a picture of an experiment result of agarose gel electrophoresis of the PCR experiment of the experimental example D-3. A leftmost column is a DNA Ladder, which has DNA segments of different lengths to serve as a reference for DNA molecular weight analysis. Columns 2-5 counted from the left are DNA amplification results generated by the platform of the ABI Veriti thermal cycler, and positive signals have high brightness and are significantly different from negative signals. Columns 6-7 of FIG. 25 are results of performing the PCR by using the multi-tube single-side flat-edge type heating carrier of the experimental example B-4 in collaboration with the tubular structure according to the example 1 of the disclosure. Positive signals produce high brightness signals at the same position, indicating a result of DNA amplification, while negative signals do not have the DNA amplification signal, and signal interpretations are all correct.

Experimental Example D-4: Comparison of PCR Test Results Under Different Conditions In the experiment example D-4, the PCR test results of different systems and different tubes under different operating conditions are compared. In the experimental example D-4, a commercial PCR tube (purchased from Axygen; model No. PCR-02-C) and a tubular structure of the example 1 are respectively placed in the multi-tube single-side flat-edge type heating carrier of the experimental example B-4 equipped with the temperature control device for performing the PCR experiment. Meanwhile, a 96-well PCR thermal cycler (Applied Biosystems Inc., Veriti) is used to perform a reagent verification test.

First, 20 μL of the mineral oil (CAS No. 8042-47-5; purchased from Tedia) and 10 μL of the reagent solution B are filled in each tube. Then, the PCR experiment is performed according to the experimental operating parameters of the table 5. After the PCR experiment is completed, agarose gel electrophoresis is applied to perform parallel comparison after the DNA amplification. The operating conditions of the experimental example D-4 and the result of agarose gel electrophoresis are shown in FIG. 27 and a following table 5.

TABLE 5

| Column | 2 | 3 | 4 | 5 | 6 | 7 | 8 | 9 | 10 | 11 | 12 | 13 | 14 |
|---|---|---|---|---|---|---|---|---|---|---|---|---|---|
| Platform | Veriti | | | | Example B-4 | | | | | | | | |
| Tube | | | Example 1 | | | | Commercial PCR tube | | | | | | |
| High temperature | 95° C. | | 96° C. | | 95° C. | | | 95° C. | | | 95° C. | | |
| Time | 20 s | | 45 s | | 10 s | | | 10 s | | | 0 s | | |
| Low temperature | 63° C. | | 63.5° C. | | 62° C. | | | 62.5° C. | | | 62° C. | | |
| Time | 45 s | | 75 s | | 40 s | | | 30 s | | | 30 s | | |
| Cycle | 35 times | | 40 times | | 35 times | | | 35 times | | | 35 times | | |
| P/N | P | N | P | P | P | P | N | P | P | N | P | P | P |

Figure 27:
FIG. 27 is a picture of an experiment result of agarose gel electrophoresis of a PCR experiment of an experimental example D-4.

FIG. 27 is a picture of an experiment result of agarose gel electrophoresis of the PCR experiment of the experimental example D-4. A leftmost column of FIG. 27 is a DNA Ladder, which has DNA segments of different lengths to serve as a reference for DNA molecular weight analysis. Columns 2-3 counted from the left are DNA amplification results generated by the platform of the ABI Veriti thermal cycler, and positive signals have high brightness and are significantly different from negative signals. Columns 4-5 counted from the left are results of DNA amplification generated by using the heating carrier and the tubular structure according to the disclosure. Positive signals generated by using the tubular structure of the example 1 and the multi-tube single-side flat-edge type heating carrier of the experimental example B-4 are clear. Then, columns 6-14 counted from the left are DNA amplification results produced by using the multi-tube single-side flat-edge type heating carrier of the experimental example B-4 and a commercial PCR tube (purchased from Axygen; model No. PCR-02-C) under different thermal cycling operating conditions, wherein in the columns 6-8, each of the tubes may generate the correct DNA amplification signal under a high temperature of 95° C., a high temperature holding time of 10 s, a low temperature of 62° C., a low temperature holding time of 40 s, and a thermal cycling times of 35; in the columns of 9-11, the low temperature is changed to 62.5° C. and the low temperature holding time is shortened to 30 s, and each of the tubes may also generate the correct DNA amplification signal; and in the columns 12-14, the high temperature holding time is shortened to 0 s, and the low temperature holding time is maintained, and the DNA amplification result may also be correctly interpreted.

This series of experiments prove that by using the heating carriers of the disclosure in collaboration with the commercial PCR tube and the tubular structures of the disclosure, the result of DNA amplification may all be achieved.

In summary, the disclosure provides a tubular structure for ddPCR and a method of using the tubular structure to produce droplets. The tubular structure may be used for droplet generation, polymerase chain reaction and/or detection, which reduces consumption of consumables of the ddPCR, simplifies a flow of the ddPCR, and reduces the cost of the ddPCR.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A tubular structure for producing droplets, comprising:
a reagent containing region, disposed on a middle portion of an upper portion inside the tubular structure and extending along a tube body length direction;
a first microchannel disposed inside the tubular structure and located below the reagent containing region, and the first microchannel extending along the tube body length direction;
an oil filling channel and an exhaust channel, disposed at the upper portion inside the tubular structure and are respectively located at two opposite sides of the reagent containing region, wherein the oil filling channel and the exhaust channel extend along the tube body length direction;
an oil storage region, disposed at a lower portion inside the tubular structure, wherein the oil filling channel is connected above the oil storage region and communicates with the oil storage region;
a droplet containing region, disposed at the lower portion inside the tubular structure, wherein the exhaust channel is connected above the droplet containing region and communicates with the droplet containing region;
a second microchannel, located between the oil storage region and the droplet containing region and connected to the oil storage region and the droplet containing region, wherein the second microchannel extends along a radial direction perpendicular to the tube body length direction, one end of the first microchannel is vertically connected to the second microchannel, and the second microchannel communicates with the oil storage region, the droplet containing region and the first microchannel.

2. The tubular structure for producing droplets as claimed in claim 1, wherein the second microchannel is located at a bottom portion inside the tubular structure, the first microchannel is located between the oil storage region and the droplet containing region and extends below the reagent containing region along the tube body length direction to the bottom portion inside the tubular structure to connect the second microchannel.

3. The tubular structure for producing droplets as claimed in claim 1, wherein a bottom surface of the tubular structure is a smooth flat surface.

4. The tubular structure for producing droplets as claimed in claim 1, wherein the second microchannel is located at a top surface of the oil storage region and the droplet containing region, and the first microchannel extends below the reagent containing region along the tube body length direction to connect the second microchannel.

5. The tubular structure for producing droplets as claimed in claim 4, further comprising a transparent block located between the oil storage region and the droplet containing region and located below the second microchannel, wherein the transparent block extends below the second microchannel along the tube body length direction to a bottom portion of the tubular structure.

6. The tubular structure for producing droplets as claimed in claim 1, wherein a first end of the second microchannel is connected to the oil storage region, a second end of the second microchannel opposite to the first end is connected to the droplet containing region, and the one end of the first microchannel is vertically connected to the second end of the second microchannel.

7. The tubular structure for producing droplets as claimed in claim 1, wherein a diameter of the first microchannel is less than a diameter of the second microchannel.

8. The tubular structure for producing droplets as claimed in claim 1, wherein a first end of the second microchannel is connected to the oil storage region, a second end of the second microchannel opposite to the first end is connected to the droplet containing region, and the one end of the first microchannel is vertically connected to a middle portion of the second microchannel between the first end and the second end.

9. The tubular structure for producing droplets as claimed in claim 1, wherein oil is pre-sealed in the oil storage region.

10. A tubular structure for producing droplets, comprising:
a reagent containing inner tube, disposed at a middle portion inside the tubular structure and extending along a tube body length direction, wherein the reagent containing inner tube has a first cavity to contain a reagent solution, and the reagent containing inner tube comprises a microwell array located at a lower portion of the reagent containing inner tube; and
an oil agent containing outer tube, located outside the reagent containing inner tube and surrounding a side portion of the reagent containing inner tube and the lower portion of the reagent containing inner tube, wherein the oil agent containing outer tube has a second cavity to contain an oil body, the microwell array is located between the reagent containing inner tube and the oil agent containing outer tube, and the reagent solution in the reagent containing inner tube is separated in the oil body in the oil agent containing outer tube to form the droplets through the microwell array.

11. The tubular structure for producing droplets as claimed in claim 10, wherein a diameter of a micropore of the microwell array is 0.05 mm to 0.5 mm.

12. A method for producing droplets, comprising:
providing a tubular structure, and the tubular structure comprising a reagent containing region, an oil agent containing region, a droplet containing region, a first microchannel and a second microchannel disposed inside the tubular structure, wherein the first microchannel is connected below the reagent containing region and communicates with the reagent containing region, the second microchannel is connected between the oil agent containing region and the droplet containing region and communicates with the oil agent containing region and the droplet containing region, the first microchannel is vertically connected to the second microchannel, and the first microchannel and the second microchannel communicate with each other;
adding a reagent solution containing a specimen to the reagent containing region;
adding an oil agent to the oil agent containing region; and
driving the reagent solution to pass through the first microchannel, and driving the oil agent to flow into the second microchannel, such that the oil agent wraps the reagent solution to form reagent-in-oil droplets.

13. The method for producing droplets as claimed in claim 12, wherein the driving the reagent solution to pass through the first microchannel and driving the oil agent to flow into the second microchannel comprises: using a power source along with air to pressurize and drive the reagent solution to pass through the first microchannel and simultaneously pressurize and drive the oil agent to flow into the second microchannel, so that the oil agent wraps the reagent solution to form the reagent-in-oil droplets in the droplet containing region.

14. The method for producing droplets as claimed in claim 12, wherein the driving the reagent solution to pass through the first microchannel and driving the oil agent to flow into the second microchannel comprises: using a power source along with air to pressurize and drive the reagent solution to pass through the first microchannel and simultaneously pressurize and drive the oil agent to flow into the second microchannel, so that the oil agent wraps the reagent solution to form the reagent-in-oil droplets in the second microchannel.

15. The method for producing droplets as claimed in claim 12, wherein the tubular structure is heated when driving the reagent solution to pass through the first microchannel and driving the oil agent to flow into the second microchannel.

16. The method for producing droplets as claimed in claim 12, wherein the oil agent is pre-sealed in the oil agent containing region before the reagent solution is added.

17. The method for producing droplets as claimed in claim 12, wherein the specimen comprises a biological specimen, biomolecules, nano particles, viruses, a food specimen or an environmental specimen.

18. The method for producing droplets as claimed in claim 17, further comprising detecting the droplets containing the reagent solution in an optical manner.

19. The method for producing droplets as claimed in claim 17, further comprising detecting the droplets containing the reagent solution in an electromagnetic manner, wherein the specimen further comprises a magnetic label.

20. The method for producing droplets as claimed in claim 12, further comprising performing a thermal cycling reaction on the droplets containing the reagent solution, wherein the specimen comprises nucleotide molecules or deoxynucleotide molecules, the reagent solution comprises a polymerase chain reaction (PCR) reagent, and a polymerase chain reaction (PCR) is performed in the droplets.

* * * * *